United States Patent [19]

Biftu et al.

[11] Patent Number: 5,792,776
[45] Date of Patent: Aug. 11, 1998

[54] COMPOUNDS AND METHODS FOR THE TREATMENT OF CARDIOVASCULAR, INFLAMMATORY AND IMMUNE DISORDERS

[75] Inventors: Tesfaye Biftu, Belmont; Ralph Scannell, Hopkinton; Xiong Cai, Framingham; Sajjat Hussoin, Lexington, all of Mass.

[73] Assignee: Cytomed, Inc.,, Cambridge, Mass.

[21] Appl. No.: 265,656

[22] Filed: Jun. 27, 1994

[51] Int. Cl.⁶ ............... A61K 31/44; A61K 31/40; C07D 307/02; C07C 233/00

[52] U.S. Cl. ............... 514/303; 514/423; 514/445; 514/448; 514/471; 514/575; 514/613; 514/618; 514/621; 546/118; 548/304.7; 548/530; 549/72; 549/77; 549/487; 549/66; 562/621; 564/161; 564/182; 564/189

[58] Field of Search ............... 549/496, 493, 549/475, 472, 484, 488, 487, 77, 73, 72, 62, 67, 64, 66, 65; 514/471, 445, 446, 448, 438, 423, 617, 613, 618, 619, 575, 303; 548/530, 304.7; 564/189, 182, 161–163, 168; 562/621; 546/118

[56] References Cited

U.S. PATENT DOCUMENTS

| | | | |
|---|---|---|---|
| 2,690,988 | 10/1954 | Jones et al. | 167/33 |
| 4,166,452 | 9/1979 | Generales, Jr. | 128/741 |
| 4,256,108 | 3/1981 | Theeuwes | 128/260 |
| 4,265,874 | 5/1981 | Bonsen et al. | 424/15 |
| 4,522,811 | 6/1985 | Eppstein et al. | 514/2 |
| 4,539,332 | 9/1985 | Biftu et al. | 514/461 |
| 4,595,693 | 6/1986 | Biftu et al. | 514/461 |
| 4,604,407 | 8/1986 | Haslanger et al. | 514/575 |
| 4,656,190 | 4/1987 | Shen et al. | 514/529 |
| 4,757,084 | 7/1988 | Biftu et al. | 514/438 |
| 4,841,968 | 6/1989 | Dunn et al. | 128/335.5 |
| 4,845,129 | 7/1989 | Anderson et al. | 514/600 |
| 4,871,756 | 10/1989 | Gillard et al. | 514/381 |
| 4,873,259 | 10/1989 | Summers, Jr. et al. | 514/443 |
| 4,876,346 | 10/1989 | Musser et al. | 546/172 |
| 4,891,363 | 1/1990 | Nakamura et al. | 514/94 |
| 4,910,206 | 3/1990 | Houlihan | 514/292 |
| 4,916,145 | 4/1990 | Tilley et al. | 514/357 |
| 4,959,361 | 9/1990 | Walser | 514/220 |
| 4,987,132 | 1/1991 | Mase et al. | 514/252 |
| 4,992,428 | 2/1991 | Houlihan et al. | 514/63 |
| 4,996,203 | 2/1991 | Biftu et al. | 514/235.2 |
| 5,001,123 | 3/1991 | Biftu et al. | 514/231.5 |
| 5,037,853 | 8/1991 | Brooks et al. | 514/595 |
| 5,047,420 | 9/1991 | Graham et al. | 514/484 |
| 5,110,831 | 5/1992 | Magolda et al. | 514/645 |
| 5,112,848 | 5/1992 | Brooks et al. | 514/424 |
| 5,169,854 | 12/1992 | Brooks et al. | 514/314 |
| 5,175,183 | 12/1992 | Brooks et al. | 514/438 |
| 5,183,818 | 2/1993 | Brooks et al. | 514/231.5 |
| 5,187,192 | 2/1993 | Brooks et al. | 514/445 |
| 5,234,950 | 8/1993 | Edwards et al. | 514/473 |
| 5,244,896 | 9/1993 | Borcherding et al. | 514/258 |
| 5,288,751 | 2/1994 | Brooks et al. | 514/438 |
| 5,296,494 | 3/1994 | Lavrelle et al. | 514/343 |
| 5,326,787 | 7/1994 | Brooks et al. | 514/507 |
| 5,334,616 | 8/1994 | Mueller et al. | 514/473 |
| 5,344,843 | 9/1994 | Guthrie et al. | 514/473 |
| 5,358,938 | 10/1994 | Cai et al. | 514/231.5 |
| 5,420,164 | 5/1995 | Mishina et al. | 514/596 |
| 5,434,151 | 7/1995 | Cai et al. | 514/231.5 |
| 5,463,083 | 10/1995 | Biftu et al. | 549/71 |
| 5,561,134 | 10/1996 | Spada et al. | 514/266 |

FOREIGN PATENT DOCUMENTS

| | | |
|---|---|---|
| 0 144 804 | 6/1985 | European Pat. Off. |
| 0 199 324 | 10/1986 | European Pat. Off. |
| 0 217 204 | 4/1987 | European Pat. Off. |
| 0 252 823 A1 | 1/1988 | European Pat. Off. |
| 0 257 921 | 3/1988 | European Pat. Off. |
| 0 319 947 A2 | 6/1989 | European Pat. Off. |
| 0 322 033 | 6/1989 | European Pat. Off. |
| 0 338 993 A1 | 10/1989 | European Pat. Off. |
| 0 365 089 A2 | 4/1990 | European Pat. Off. |
| 0 367 110 A1 | 5/1990 | European Pat. Off. |
| 0 388 309 A2 | 9/1990 | European Pat. Off. |
| 0 402 150 A1 | 12/1990 | European Pat. Off. |
| 0 402 151 A1 | 12/1990 | European Pat. Off. |
| 0 402 155 | 12/1990 | European Pat. Off. |
| 0 402 156 | 12/1990 | European Pat. Off. |
| 0 416 609 A2 | 3/1991 | European Pat. Off. |
| 0 617 032 | 9/1994 | European Pat. Off. |
| 3701344 A1 | 7/1987 | Germany. |
| 3724031 A1 | 1/1988 | Germany. |
| 3724164 A1 | 1/1988 | Germany. |
| 3936828 A1 | 5/1990 | Germany. |
| 4006471 A1 | 9/1990 | Germany. |
| 2 197 650 | 5/1988 | United Kingdom. |
| 2 233 974 | 1/1991 | United Kingdom. |
| 2 263 109 | 7/1993 | United Kingdom. |
| WO 89/04299 | 5/1989 | WIPO. |
| WO 90/12015 | 10/1990 | WIPO. |
| WO 91/17157 | 11/1991 | WIPO. |

(List continued on next page.)

OTHER PUBLICATIONS

Leonard et al, "Amides of 1-methyl-5-(3,4-dimethoxyphenyl)pyrrolidine-2 emboxylic acid", Cai :70485 (1969).

(List continued on next page.)

*Primary Examiner*—Deborah C. Lambkin
*Attorney, Agent, or Firm*—Kilpatrick Stockton LLP

[57] ABSTRACT

Disubstituted tetrahydrofurans, tetrahydrothiophenes, pyrrolidines and cyclopentanes are disclosed that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i. e., by acting as both a PAF receptor antagonist and inhibitor of 5-lipoxygenase.

A method to treat disorders mediated by PAF and/or leukotrienes is also disclosed, that includes administering an effective amount of one or more of the above-identified compounds or a pharmaceutically acceptable salt thereof, optionally in a pharmaceutically acceptable carrier.

30 Claims, No Drawings

FOREIGN PATENT DOCUMENTS

| | | |
|---|---|---|
| WO 92/09566 | 6/1992 | WIPO. |
| 9213848 | 8/1992 | WIPO. |
| WO 92/15294 | 9/1992 | WIPO. |
| WO 93/01191 | 1/1993 | WIPO. |
| WO 93/16075 | 8/1993 | WIPO. |
| WO 94/01430 | 1/1994 | WIPO. |
| WO 94/04537 | 3/1994 | WIPO. |
| WO 94/06790 | 3/1994 | WIPO. |
| WO 95/18610 | 7/1995 | WIPO. |
| WO 96/00212 | 7/1996 | WIPO. |

OTHER PUBLICATIONS

Bartroli, J., "Design of Potent Linear PAF Antagonists," *J. Med. Chem.*, vol. 34 (1991) pp. 3328–3334.

Biftu, T., et al., "Confirmation and Activity of Tetrahydrofuran Lignans and Analogues as Specific Platelet Activating Factor Antagonists," *J. Med. Chem.* vol., 29, No. 10 (1986) pp. 1917–1921.

Caricellar, E., et al., "4–Substituted 2–Alkoxytetrahydrofurans as Potent and Long–Lasting PAF Antagonists," *J. Med. Chem.*, vol. 35 (1992) pp. 676–683.

Corey, F. J., et al., "Dual Binding Modes to the Receptor for Platelet Activating Factor (PAF) of Anti–PAF Trans–2, 5–Diarylfurans," *Tetrahedron Letters*, vol. 29, No. 24 (1988) pp. 2899–2902.

Crawley, G.C., "Methoxytetrahydropyrans. A New Series of Selective and Orally Potent 5–Lipoxygenase Inhibitors," *J. Med. Chem.*, vol. 35, No. 14 (1992) pp. 2600–2609.

Feinmark, S. J., "Leukotriene C Biosynthesis during Polymorphonuclear Leukocyte–Vascular Cell Interactions," *Methods in Enzymology*, vol. 187, pp. 559–560, (1990).

Graham, D.W., et al., "1,3–Diarylcyclopentanes: A New Class of Potent PAF Receptor Antagonists,", 197th ACS National Meeting, Division of Medicinal Chemistry, Poster No. 25, Dallas, Texas (Apr., 1989).

Guthrie, R.W., et al., "Propenyl Carboxamide Derivatives As Antagonists of Platelet Activating Factor," *J. Med. Chem.*, vol. 33 (1990) pp. 2856–2864.

Hwang, S., "Specific Receptors of Platelet–Activating Factor, Receptor Heterogeneity, and Signal Transduction Mechanisms," *J. Lipid Mediators*, vol. 2 (1990) pp. 123–158.

Lave, D., et al., "Pyrrolo[1,2–c]Thiazole Derivatives: Potent PAF Receptor Antagonists," *Drugs of the Future*, vol. 14, No. 9 (1989) pp. 891–898.

McColl, S.R., "Determination of 5–Lipoxygenase Activity in Human Polymorphonuclear Leukocytes Using High–Performance Liquid Chromatography," *J. Chromatography*, vol. 378 (1986) pp. 44–449.

Musser, J.H., et al., "5–Lipoxygenase: Properties, Pharmacology, and the Quinolinyl(bridge)aryl Class of Inhibitors," *J. Med. Chem.*, vol. 35, No. 14 (1992) pp. pp. 2502–2524.

O'Donnell, M., et al., "Comparison of the Pulmonary Pharmacology of Leukotrienes and PAF: Effects of their Antagonists," *Therapeutic Approaches to Inflammatory Diseases* Proceedings of the Fourth International Conference of the Inflammatory Research Association, Oct. 23–27, 1988, White Haven, Pennsylvania, p. 169.

Ogiso, A., et al., "The Structure of Futoenone, A Novel Spiro–Cyclohexadienone Derivative," *Tetrahedron Letters*, No. 16, (1968) pp. 2003–2008.

Ogiso, A., et al., "The Structure and Total Synthesis of Futoenone, a Constitute of *Piper futokadzura* SIEB. et ZUCC.," *Chem. Pharm. Bull.*, vol. 18, No. 1, (1970) pp. 105–114.

Page, C., et al., "PAF: New Antagonists: New Roles in Diseases and a Major Role in Reproductive Biology." *3rd International Conference on Platelet–Activating Factor and Structurally Related Alkyl Ether Lipids*, Tokyo, Japan, May 8–12, 1989.

Ponpipom, M.M., et al., "Structure–Activity Relationships of Kadsurenone Analogues," *J. Med. Chem.*, vol. 30 (1987) pp. 136–142.

Ponpipom, M.M., et al., "(±)–TRANS–2–(3–Methylsulfonyl–4–Propoxyphenyl)–5–(3,4,5–Trimethoxyphenyl)Tetrahydrofuran (L–659,989), A Novel, Potent PAF Receptor Antagonist," *Biochemical and Biophysical Research Communications*, vol. 150, No. 3 (1988) pp. 1213–1220.

Shen, T.Y., "Characterization of a Platelet–Activating Factor Receptor Antagonist Isolated from Halifenteng (*Piper futokadsura*): Specific Inhibition of in vitro and in vivo Platelet–Activating Factor–Induced Effects," *Proc. Natl. Acad. Sci. USA*, vol. 82, (Feb. 1985) pp. 672–676.

Shen, T.Y., et al., "The Chemical and Biological Properties of PAF Agonists, Antagonists, and Biosynthetic Inhibitors," *Platelet–Activating Factor and Related Lipid Mediators*, Plenum Press, New York, NY, pp. 153–190, (1986).

Weber, K.H., et al., "Hetrazepines as Antagonists of Platelet Activating Factor," *Medicinal Research Reviews*, vol. 9, No. 1 (Jan.–Mar. 1989) pp. 181–218.

Communication dated Mar. 4, 1997 in European Patent App. No. 95907972.4.

Backvall, et al., "A Stereocontrolled Organopalladium Route to 2,5–Disubstituted Pyrrolidine Derivatives. Application to the Synthesis of a Venom Alkaloid of the Ant Species *Monomorium latinode*," *J. Org. Chem.*, 55:826–831 (1990).

Biftu, T., et al., *Abstr. of 6th Int. Conf. on Prostaglandins and Related Compounds*, Florence, Italy, p. 302 (Jun. 3–6, 1986).

Bowles, et al., A Convenient Preparation of Cyclic Ether Acetals Mediated by Trifluoroacetic Anhydride, *Synlett*, pp. 111–112 (1993).

Carter, et al., "5–Lipoxygenase Inhibitory Activity of Zileuton," *J. of Pharmacol. and Exp. Thera.*, 256(3);929–937 (1991).

Danyoshi et al., "Pyrrolidine Derivatives as Inhibitors of Platelet Aggregation Induced by Platelet Activating Factor," *Chem. Pharm. Bull.*, 37(7):1969–1970 (1989).

Erez, et al., "Narcotic Antagonistic Potency of Bivalent Ligands Which Contain Beta–Naltrexamine. Evidence for Bridging between Proximal Recognition Sites," *J. of Med. Chem.*, 25(7):847–849 (1982).

Foye, (Editor) "Bioisosterism," *Principles of Med. Chem.*, Second Edition, pp. 80–81 (Lea & Febiger, Philadelphia, 1981).

Goldstein, et al., "Dual Inhibitors of Platelet Activating Factor and 5–Lipoxygenase. I., 2,40Diaryl–1,3–dithiolanes," *Med. Chem. Res.*, 2:443–450 (1992).

Goldstein, et al., "Dual Inhibitors of Platelets Activating Factor and 5–Lipoxygenase. II. Novel 2,4–Diaryl–1,3–dithiolanes with Iron–Chelating Functionalities," *Med. Chem. Res.*, 2:451–456 (1992).

Hwang, S., et al., "*Trans*–2, 5–bis–(3,4,5–trimethoxyphenyl)tetrahydrofuran," *Journal of Biological Chemistry*, 260(29):15639–15645 (1985).

Hwang, S., et al., "Biochemical and Pharmacological Characterization of L-659,989: An Extremely Potent, Selective and Competitive Receptor Antagonist of Platelet-Activating Factor," *J. Pharmacol. Ther.*, 246(2):534-541 (1988).

Ikeda et al., "Preparation of Hydroxamic Acid and N-Hydroxyurea Derivatives and Their Use as Lipoxygenase Inhibitors," *Chemical Abstracts*, vol. 118, Abstract No. 59426 (1993).

Page, C., et al., "PAF: New Antagonists, New Roles in Diseases and a Major Role in Reproductive Biology," *Trends in Pharmacol. Sci.*, pp. 256-257 (1989).

Sahoo, et al., "Synthesis and Biological Activity of MK 287 (L-680,573): A Potent, Specific, and Orally Active PAF Receptor Antagonist," *Bioorg. & Med. Chem. Lett.*, 1(6):327-332 (1991).

Schwenk, et al., "Identification of 5-Oxo-15-hydroxy-6,8,11,13-eicosatetraenoic Acid as a Novel and Potent human Eosinophil Chemotactic Eicosanoid," *J. Biol. Chem.* 267(18):12482-12488 (1992).

Seminaro and Gleich, "The role of eosinophils in the pathogenesis of asthma," *Curr. Opin. in Immunol.*, 6:860-864 (1994).

Shen and Hussaini, "Kadsurenone and Other Related Lignans as Antagonists of Platelet-Activating Factor Receptor," *Methods of Enzymol.*, 187:446-454 (1990).

Shizuri, et al., "Synthesis of some physiologically active substances using anodic oxidation of phenols as a key-step," *Tennen Yuki Kagobustu Toronkai Koen Yoshishu, Chem. Abstracts*, Abstract 209491p (1983).

Talapatra, et al., "Maglifloenone,a novel spirocyclohexadienone neolignan and other constituents from Magnolia liliflora," *Chem. Abstracts*, Abstract No. 52493k (1982).

Terashita, et al., "CV-3988 -A Specific Antagonist of Platelet Ativating Factor (PAF)," *Life Sciences*, 32(17):1975-1982 (1983).

Wood, et al., "Cyclic Ether Acetal Platelet Activating Factor (PACF) Receptor Antagonists II: Imidazo[4,5-c]Pyridyl Derivatives," *Bioorg. & Med. Chem. Lett.*, 3(8):1499-1504 (1993).

Yeadon, et al., "Effect of BW B70C, a novel inhibitor of arachidonic acid 5-lipoxygenase, on allergen-induced bronchoconstriction and late-phase lung eosinophil accumulation in sensitised guinea-pigs," *Agents and Actions*, 38:8-18 (1993).

COMPOUNDS AND METHODS FOR THE TREATMENT OF CARDIOVASCULAR, INFLAMMATORY AND IMMUNE DISORDERS

FIELD OF THE INVENTION

This invention is in the area of 2,5-disubstituted tetrahydrothiophenes, tetrahydrofurans, pyrrolidines and 1,3-disubstituted cyclopentanes. The compounds exhibit biological activity by acting as PAF receptor antagonists, by inhibiting the enzyme 5-lipoxygenase, or by exhibiting dual activity, i. e., by acting as both a PAF receptor antagonist and inhibitor of 5-lipoxygenase.

BACKGROUND OF THE INVENTION

Platelet activating factor (PAF, 1-O-alkyl-2-acetyl-sn-glycerol-3-phosphorylcholine) is a potent inflammatory phospholipid mediator with a wide variety of biological activities. PAF was initially identified as a water soluble compound released by immunoglobulin E (IgE)-sensitized rabbit basophils. It is now known that PAF is also generated and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. (Hwang, "Specific receptors of platelet-activating factor, receptor heterogeneity, and signal transduction mechanisms", *Journal of Lipid Mediators* 2, 123 (1990)). PAF causes the aggregation and degranulation of platelets at very low concentrations. The potency (active at $10^{-12}$ to $10^{-9}$M), tissue level (picomoles) and short plasma half life (2–4 minutes) of PAF are similar to those of other lipid mediators such as thromboxane $A_2$, prostaglandins, and leukotrienes.

PAF mediates biological responses by binding to specific PAF receptors found in a wide variety of cells and tissues. Structure-activity studies on PAF and its analogs indicate that the ability of PAF to bind to these receptors is structure specific and stereospecific. (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987)).

While PAF mediates essential biological responses, it also appears to play a role in pathological immune and inflammatory responses. Many published studies have provided evidence for the involvement of PAF in human diseases, including arthritis, acute inflammation, asthma, endotoxic shock, pain, psoriasis, ophthalmic inflammation, ischemia, gastrointestinal ulceration, myocardial infarction, inflammatory bowel diseases, and acute respiratory distress syndrome. Animal models also demonstrate that PAF is produced or increased in certain pathological states.

The involvement of PAF in pathological inflammatory and immune states has stimulated a substantial research effort to identify PAF receptor antagonists. In 1983, a phospholipid analog referred to as CV-3988 (rac-3-(N-n-octadecyl-carbamoyloxy-ω-methoxypropyl-2-thiazolioethyl phosphate) was reported to have PAF receptor antagonist properties. (Terashita, et al., *Life Sciences* 32, 1975 (1983).) In other early work in this area, Shen, et al., (in *Proc. Natl. Acad. Sci. (U.S.A.)* 82, 672 (1985)), reported that kadsurenone, a neolignan derivative isolated from Piper futokadsura Sieb et Zucc (a Chinese herbal plant) was a potent, specific and competitive inhibitor of PAF activity at the receptor level.

Hwang, et al., disclosed in 1985 that trans-2,5-bis-(3,4,5-trimethoxyphenyl) tetrahydrofuran (L-652, 731) inhibits the binding of tritiated PAF to PAF receptor sites. (Hwang, et al., "Trans-2,5-bis-(3,4,5-trimethoxyphenyl) tetrahydrofuran", *Journal of Biological Chemistry* 260, 15639 (1985).) L-652,731 was found to be orally active, and to inhibit PAF-induced rat cutaneous vascular permeability at a dosage of 30 mg/kg body weight. The compound was found to have no effect on the enzyme 5-lipoxygenase. Hwang, et al. also reported that trans-L-652,731 (wherein the aryl groups at the 2 and 5 positions are on opposite sides of the plane of the tetrahydrofuran ring) is approximately 1000 times more potent than cis-L-652,731 (wherein the 2 and 5 aryl substituents are on the same side of the plane of the tetrahydrofuran ring).

In 1988, Hwang, et al., reported that L-659,989 (trans-2-(3-methoxy-4-propoxyphenyl-5-methylsulfonyl)-5-(3,4,5-trimethoxyphenyl)tetrahydrofuran) is an orally active, potent, competitive PAF receptor antagonist, with an equilibrium inhibition constant 10 times greater than that of trans-L-652,731. (Hwang, et al., *J. Pharmacol. Ther.* 246, 534 (1988).)

U.S. Pat. Nos. 4,996,203, 5,001,123 and 4,539,332 to Biftu, et al. and European Patent Application Nos. 89202593.3, 90306235.4, and 90306234.7 disclose that specific classes of 2,5-diaryl tetrahydrofurans are PAF receptor antagonists.

Bowles et al., *Synlett*, 1993, pp 111 disclose a limited number of substituted tetrahydrofurans which may possess PAF receptor antagonism.

Danyoshi et al., *Chem. Pharm. Bull.*, 1989, pp 1969, disclose 2-substituted-N-alkoxycarbonyl pyrrolidines which inhibit PAF induced rabbit platelet aggregation.

Leukotrienes, like PAF, are potent local mediators, playing a major role in inflammatory and allergic responses, including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase to the hydroperoxide 5-hydroperoxyeicosatetraenoic acid (5-HPETE), that is converted to leukotriene $A_4$, that in turn can be converted to leukotriene $B_4$, $C_4$, or $D_4$. The slow-reacting substance of anaphylaxis is now known to be a mixture of leukotrienes $C_4$, $D_4$, and $E_4$, all of which are potent bronchoconstrictors. There has been a research effort to develop specific receptor antagonists or inhibitors of leukotriene biosynthesis, to prevent or minimize pathogenic inflammatory responses mediated by these compounds.

Leukotrienes are released simultaneously from leukocytes with PAF, possibly from a common phospholipid precursor such as 1-O-hexadecyl-2-arachidonyl-sn-glycerophosphocholine, and upon cellular activation, act synergistically with PAF in many biological models. European Patent Application Nos. 90117171.0 and 901170171.0 disclose indole, benzofuran, and benzothiophene lipoxygenase inhibiting compounds.

Recently, it was reported that the tetrahydrothiophene derivative of L-652,731, trans-2,5-bis-(3,4,5-trimethoxyphenyl)tetrahydrothiophene (L-653,150), is a potent PAF antagonist and a moderate inhibitor of 5-lipoxygenase. It has been disclosed that certain 2,5-diaryl tetrahydrothiophenes are PAF antagonists and leukotriene synthesis inhibitors. (Biftu, et al., *Abstr. of 6th Int. Conf. on Prostaglandins and Related Compounds*, Jun. 3–6, 1986, Florence, Italy; U.S. Pat. No. 4,757,084 to Biftu); Wo 92/15294; WO 94/01430; WO 94/04537; and WO 94/06790.

Given the significant number of pathological immune and inflammatory responses that are mediated by PAF and leukotrienes, there remains a need to identify new compounds and compositions that exhibit PAF receptor antagonistic activity or inhibit the enzyme 5-lipoxygenase.

Therefore, it is an object of the present invention to provide compounds that reduce the chemotaxis and respiratory burst leading to the formation of damaging oxygen radicals during an inflammatory or immune response.

It is another object of the present invention to provide pharmaceutical compositions for the treatment of pathological immune or inflammatory disorders mediated by PAF or products of 5-lipoxygenase.

It is another object of the present invention to provide a method for the treatment of pathological immune or inflammatory disorders mediated by PAF or products of 5-lipoxygenase.

SUMMARY OF THE INVENTION

Compounds of Formula I are provided

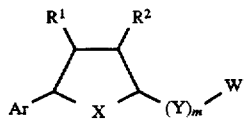

wherein:

Ar is an aryl or heteroaryl group that is optionally substituted, preferably with halo (including but not limited to fluoro), lower alkoxy (including methoxy), lower aryloxy (including phenoxy), W, cyano, or $R^3$;

m is 0 or 1;

W is independently —AN(OM)C(O)N($R^3$)$R^4$, —AN($R^3$)C(O)N(OM)$R^4$, —AN(OM)C(O)$R^4$, —AC(O)N(OM) $R^4$, —C(O)N(OM)$R^4$, —C(O)NHA, —A—B;

A is lower alkyl, lower alkenyl, lower alkynyl, alkaryl or aralkyl groups, wherein one or more carbons optionally can be replaced by O, N, or S, however, —Y—A— should not include two adjacent heteroatoms (i.e., —O—O—, —S—S—, —O—S—, etc.);

B is selected from the group consisting of pyridylimidazole and benzimidazole, either of which is optionally substituted with $R_3$, and wherein the pyridylimidazole or benzimidazole is preferably connected to A through a nitrogen atom;

M is hydrogen, a pharmaceutically acceptable cation, or a metabolically cleavable leaving group;

X is O, S, S(O), $NR^5$, or $CHR^5$;

Y is O, S, S(O), $NR^5$, or $CHR^5$;

$R^1$ and $R^2$ are independently hydrogen, lower alkyl including methyl, cyclopropylmethyl, ethyl, isopropyl, butyl, pentyl hexyl, and $C_{3-8}$ cycloalkyl, for example, cyclopentyl; halo lower alkyl, for example, trifluoromethyl; halo, for example fluoro; and —COOH;

$R^3$ and $R^4$ are independently hydrogen or alkyl, alkenyl, alkynyl, aryl, aralkyl, alkaryl, $C_{1-6}$ alkoxy-$C_{1-10}$ alkyl, $C_{1-6}$ alkylthio-$C_{1-10}$ alkyl, heteroaryl, or heteroarylalkyl-;

$R^5$ is hydrogen, lower alkyl, lower alkenyl, lower alkynyl, alkaryl, —AN(OM)C(O)N($R^3$)$R^4$, —AN($R^3$)C(O)N (OM) $R^4$, —AN(OM)C(O)$R^4$, —AC(O)N(OM)$R^4$, —AC(O)N(OM) $R^4$, —AS(O)n$R^3$, —AS(O)$_n$$CH_2$C(O)$R^3$, —AS(O)$_n$$CH_2$CH(OH)$R^3$, —AC(O)NH$R^3$; and wherein n is 0–2.

The Ar group, in one embodiment, is selected from the group consisting of phenyl, trimethoxyphenyl, dimethoxyphenyl, fluorophenyl, and specifically 4-fluorophenyl, difluorophenyl, pyridyl, dimethoxypyridyl, quinolinyl, furyl, imidazolyl, and thienyl groups.

In one embodiment, —A—B is

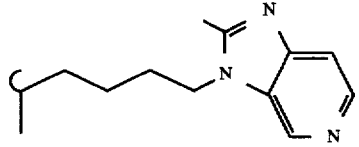

and Ar is an optionally substituted aryl or heteroaryl group, as described in more detail in section I.A. below.

These compounds in general reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

Another embodiment of the present invention is a pharmaceutical composition that includes an effective amount of a compound of Formula I or its pharmaceutically acceptable salt or derivative in combination with a pharmaceutically acceptable carrier.

A method to treat disorders mediated by PAF or leukotrienes is also disclosed, that includes administering an effective amount of one or more of the above-identified compounds or a pharmaceutically acceptable salt or derivative thereof, optionally in a pharmaceutically acceptable carrier.

Examples of immune, allergic and cardiovascular disorders include general inflammation, cardiovascular disorders including hypertension, skeletal-muscular disorders, osteoarthritis, gout, asthma, lung edema, adult respiratory distress syndrome, pain, aggregation of platelets, shock, rheumatoid arthritis, juvenile rheumatoid arthritis, psoriatic arthritis, psoriasis, autoimmune uveitis, allergic encephalomyelitis, systemic lupus erythematosis, acute necrotizing hemorrhagic encephalopathy, idiopathic thrombocytopenia, polychondrilis, chronic active hepatitis, idiopathic sprue, Crohn's disease, Graves ophthalmopathy, primary biliary cirrhosis, uveitis posterior, interstitial lung fibrosis; allergic asthma; and inappropriate allergic responses to environmental stimuli such as poison ivy, pollen, insect stings and certain foods, including atopic dermatitis and contact dermatitis.

The compounds disclosed herein can also be used as research tools to study the structure and location of PAF receptors as well as biological pathways involving leukotrienes.

The following are nonlimiting examples of compounds that fall within Formula I. These examples are merely exemplary, and are not intended to limit the scope of the invention:

2-(3,4,5-trimethoxyphenyl)-5-[3-(N'-methyl-N'-hydroxyureidyl)propoxy]tetrahydrofuran;

2-(4-fluorophenyl)-5-[3-(N'-methyl-N'-hydroxyureidyl) propoxy]tetrahydrofuran;

2-(3,4,5-trimethoxyphenyl)-5-[3-(N'-n-butyl-N'-hydroxyureidyl)-propoxy]tetrahydrofuran;

2-(4-fluorophenyl)-5-[3-(N'-n-butyl-N'-hydroxyureidyl) propoxy]tetrahydrofuran;

2-(3',4'-dimethoxyphenyl)-5-[3-(N-butyl-N-hydroxyureidyl)]-propoxytetrahydrofuran;

2-(3',4'-dimethoxyphenyl)-5-[3-(N-methyl-N-hydroxyureidyl)]-propoxytetrahydrofuran;

2-(2,4,5-trimethoxyphenyl)-5-(3-hydroxyureidylpropoxy)-tetrahydrofuran;

2-(4-fluorophenyl)-5-(3-hydroxyureidylpropoxy) tetrahydrofuran;

2-(4-fluorophenyl)-5-[3-(N'-methyl-N'-hydroxyureidyl) propoxy]tetrahydrothiophene; and 2-(4-fluorophenyl)-5-(3-hydroxyureidylpropoxy) tetrahydrothiophene.

Further nonlimiting examples of other compounds that fall within Formula I are set forth below in Tables 1 and 2.

TABLE 1

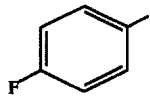

| Ar | X* | W |
|---|---|---|
| 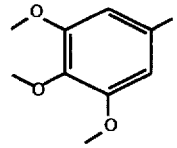 | O | CH$_2$CH$_2$CH$_2$NHC(O)N(OH)CH$_3$ |
|  | C | SAME |
| SAME | S | SAME |
| SAME | NH | SAME |
| SAME | O | CH$_2$CH$_2$CH$_2$N(OH)C(O)NH$_2$ |
| SAME | C | SAME |
| SAME | S | SAME |
| SAME | NH | SAME |
| SAME | O | CH$_2$CH$_2$CH$_2$N(OH)C(O)NHCH$_3$ |
| SAME | C | SAME |
| SAME | O | CH$_2$—CH=CH—CH$_2$N(OH)CONH$_2$ |
| 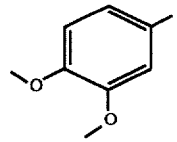 | SAME AS ABOVE | SAME AS ABOVE |
| 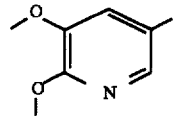 | SAME AS ABOVE | SAME AS ABOVE |
| 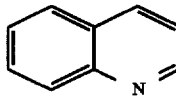 | SAME AS ABOVE | SAME AS ABOVE |
| 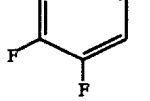 | SAME AS ABOVE | SAME AS ABOVE |

*C refers to CHR$^5$. Y is O, CHR$^5$, S, or NH.

TABLE 2

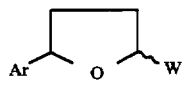

| Ar | W |
|---|---|
| 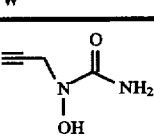 | 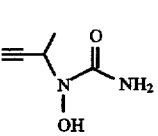 |
| same as above | 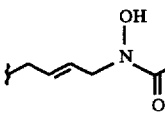 |
| same as above | 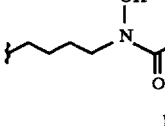 |
| same as above | 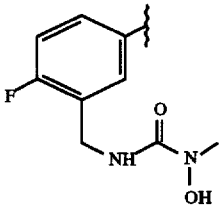 |
| 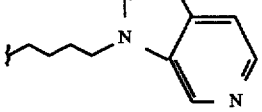 | |

DETAILED DESCRIPTION OF THE INVENTION

I. Description and Synthesis of the Compounds

A. Compounds

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to $R^3$ or one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term halo, as used herein, refers to chloro, fluoro, iodo, or bromo.

The term lower alkyl, as used herein, and unless otherwise specified, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl, optionally substituted as described above for the alkyl groups.

The term alkenyl, as referred to herein, and unless otherwise specified, refers to a straight, branched, or cyclic (in the case of $C_{5-6}$) hydrocarbon of $C_2$ to $C_{10}$ with at least one double bond, optionally substituted as described above.

The term lower alkenyl, as referred to herein, and unless otherwise specified, refers to an alkenyl group of $C_2$ to $C_6$, and specifically includes vinyl and allyl.

The term lower alkylamino refers to an amino group that has one or two lower alkyl substituents.

The term alkynyl, as referred to herein, and unless otherwise specified, refers to a $C_2$ to $C_{10}$ straight or branched hydrocarbon with at least one triple bond, optionally substituted as described above. The term lower alkynyl, as referred to herein, and unless otherwise specified, refers to a $C_2$ to $C_6$ alkynyl group, specifically including acetylenyl and propynyl.

The term aryl, as used herein, and unless otherwise specified, refers to phenyl, biphenyl, or napthyl, and preferably phenyl. The aryl group can be optionally substituted with any suitable group, including but not limited to one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, and preferably with halo (including but not limited to fluoro), lower alkoxy (including methoxy), lower aryloxy (including phenoxy), W, cyano, or $R^3$.

The term haloalkyl, haloalkenyl, or haloalkynyl refers to a alkyl, alkenyl, or alkynyl group in which at least one of the hydrogens in the group has been replaced with a halogen atom.

The term heteroaryl, heterocycle or heteroaromatic, as used herein, refers to an aromatic moiety that includes at least one sulfur, oxygen, or nitrogen in the aromatic ring, which can optionally be substituted as described above for the aryl groups. Non-limiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term aralkyl refers to an aryl group with an alkyl substituent.

The term alkaryl refers to an alkyl group that has an aryl substituent.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "metabolically cleavable leaving group" refers to a moiety that can be cleaved in vivo from the molecule to which it is attached, and includes but is not limited to an organic or inorganic anion, a pharmaceutically acceptable cation, acyl (for example (alkyl)C(O), including acetyl, propionyl, and butyryl), alkyl, phosphate, sulfate and sulfonate.

The term PAF receptor antagonist refers to a compound that binds to a PAF receptor with a binding constant of 30 µM or lower.

The term 5-lipoxygenase inhibitor refers to a compound that inhibits the enzyme at 30 µM or lower in a broken cell system.

The term pharmaceutically active derivative refers to any compound that upon administration to the recipient, is capable of providing directly or indirectly, the compounds disclosed herein.

The 2,5-disubstituted tetrahydrothiophenes, tetrahydrofurans and pyrrolidines, as well as the 1,3-disubstituted cyclopentanes described herein exhibit PAF receptor antagonist activity or inhibit the enzyme 5-lipoxygenase, or have dual activity, and are thus useful in the treatment of humans who have immune allergic or cardiovascular disorders that are mediated by PAF or products of 5-lipoxygenase.

B. Stereochemistry

The 2,5-disubstituted tetrahydrofurans, tetrahydrothiophenes, and pyrrolidines exhibit a number of stereochemical configurations. Carbon atoms 2 and 5 in the center ring are chiral, and thus the center ring exists at a minimum as a diastereomeric pair. Each diastereomer exists as a set of enantiomers. Therefore, based on the chiral $C_2$ and $C_5$ atoms alone, the compound is a mixture of four enantiomers.

If non-hydrogen substituents are located on carbon atoms 3 and 4 in the center ring, then the $C_3$ and $C_4$ atoms are also chiral, and can also exist as a diastereomeric pair, that is also a mixture of four enantiomers.

The 1,3-cyclopentanes disclosed herein also exhibit a number of stereochemical configurations. Carbon atoms 1 and 3 in the center ring are chiral, and thus the center ring exists at a minimum as a diastereomeric pair. Each diastereomer exists as a set of enantiomers. Therefore, based on the chiral $C_1$ and $C_3$ atoms alone, the compound is a mixture of four enantiomers.

If non-hydrogen substituents are located on carbon atoms 4 and 5 in the center ring, then the $C_4$ and $C_5$ atoms are also chiral, and can also exist as a diastereomeric pair, that is also a mixture of four enantiomers.

One of ordinary skill in the art can easily synthesize and separate the enantiomers of the disclosed compounds using chiral reagents and known procedures, and can evaluate the biological activity of the isolated enantiomer using methods disclosed herein or otherwise known. Through the use of chiral NMR shift reagents, polarimetry, or chiral HPLC, the optical enrichment of the compound can be determined.

Classical methods of resolution include a variety of physical and chemical techniques. Often the simplest and most efficient technique is repeated recrystallization. Recrystallization can be performed at any stage in the preparation of the compound, or the final enantiomeric product. If successful, this simple approach represents a method of choice.

When recrystallization fails to provide material of acceptable optical purity, other methods can be evaluated. If the compound is basic, one can use chiral acids that form diastereomeric derivatives that may possess significantly different solubility properties. Non-limiting examples of chiral acids include malic acid, mandelic acid, dibenzoyl tartaric acid, 3-bromocamphor-8-sulfonic acid, 10-camphorsulfonic acid, and di-p-toluoyltartaric acid. Similarly, acylation of a free hydroxyl group with a chiral acid also results in the formation of diastereomeric derivatives whose physical properties may differ sufficiently to permit separation.

Enantiomerically pure or enriched compounds can be obtained by passing the racemic mixture through a chromatographic column that has been designed for chiral separations.

C. Syntheses of Active Compounds

The 2,5-disubstituted tetrahydrofurans, tetrahydrothiophenes, and pyrrolidines disclosed herein can be prepared in a variety of ways known to those skilled in the art, including by methods disclosed by Whittaker et al, Synlett, 1993 pp 111, Biorg. Med. Lett., 1993 pp 1499; Achiwa et al., Chem. Pharm. Bull., 1989, pp. 1969.

1,3-Disubstituted cyclopentanes can be prepared using the procedure of Graham, et al. (1,3-Diaryl Cyclopentanes: A New Class of Potent PAF Receptor Antagonists. 197th ACS National Meeting, Dallas, Tex., Apr. 9–14, 1989, Division of Medicinal Chemistry, poster no. 25 (abstract)), or by other known methods.

A general procedure for preparing a hydroxyurea is shown below in Scheme 1:

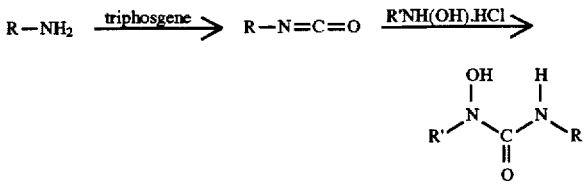

General procedures for preparing reverse hydroxyureas are shown in Scheme 2:

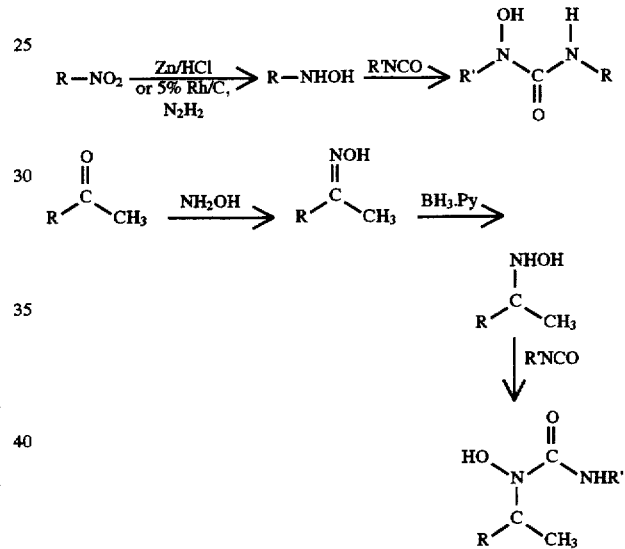

A general procedure for preparing a hydroxamic acid is shown in Scheme 3:

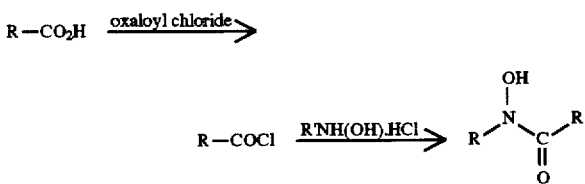

A general procedure for preparing a reverse hydroxamic acid is shown in Scheme 4:

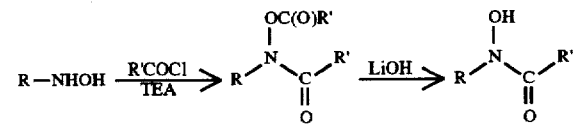

Scheme 5 shows the synthesis of 2-(3,4,5-trimethoxyphenyl)-5-[3-(N'-substituted-N'-hydroxyureidyl)

propoxy]tetrahydrofuran (1–4) and 2-(4-fluorophenyl)-5-[3-(N'-substituted-N'-hydroxyureidyl)propoxy]tetrahydrofuran (9–12):
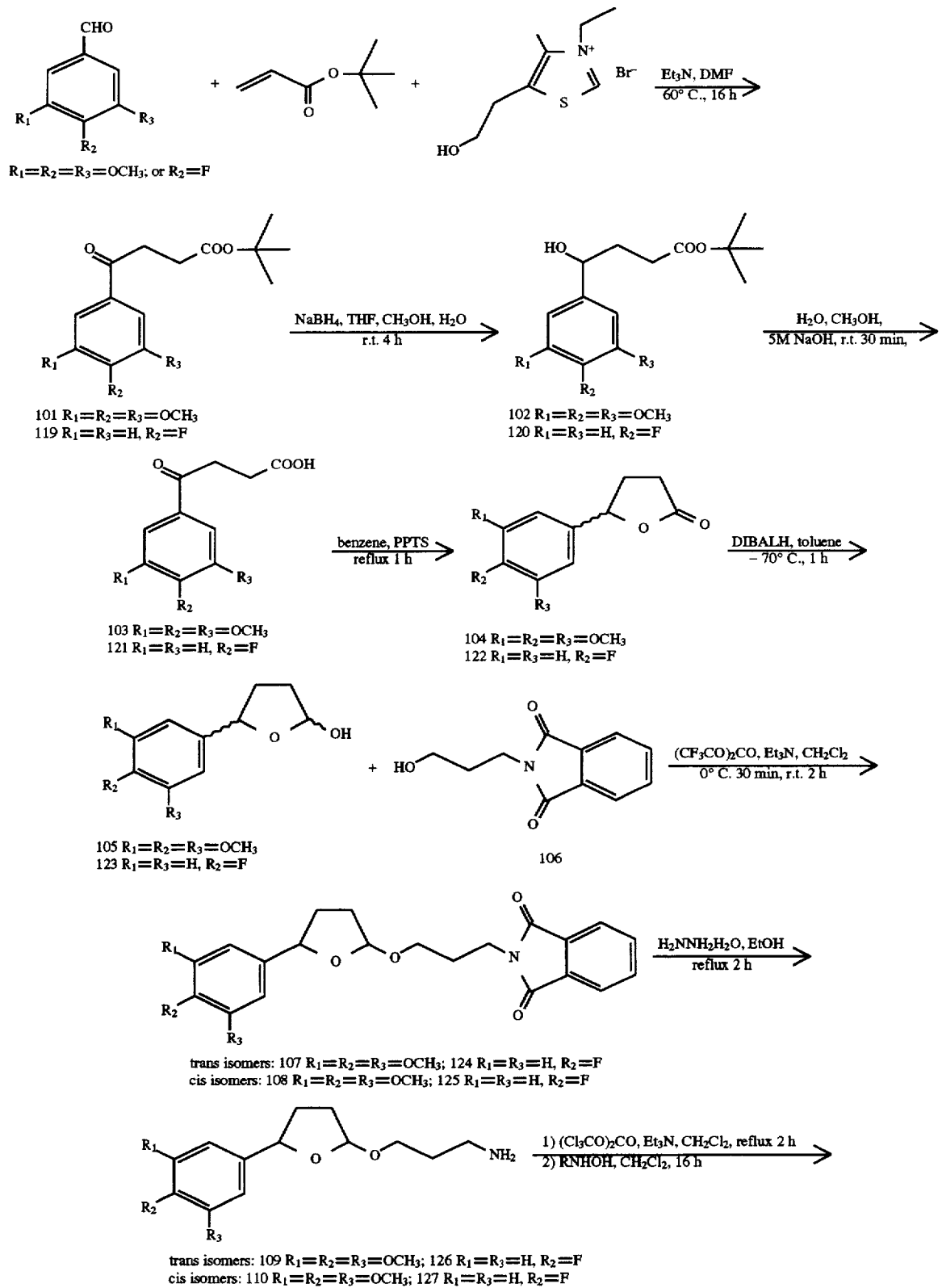
Scheme 5

-continued
Scheme 5

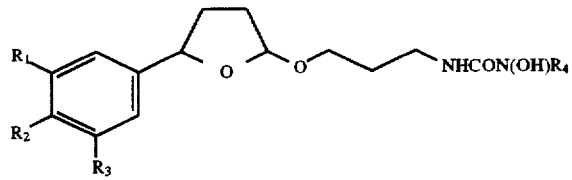

trans isomers: 1  $R_1=R_2=R_3=OCH_3$, $R_4=CH_3$
2  $R_1=R_2=R_3=OCH_3$, $R_4=CH_2CH_2CH_2CH_3$
9  $R_1=R_3=H$, $R_2=F$, $R_4=CH_3$
10  $R_1=R_3=H$, $R_2=F$, $R_4=CH_2CH_2CH_2CH_3$
cis isomers: 3  $R_1=R_2=R_3=OCH_3$, $R_4=CH_3$
4  $R_1=R_2=R_3=OCH_3$, $R_4=CH_2CH_2CH_2CH_3$
11  $R_1=R_3=H$, $R_2=F$, $R_4=CH_3$
12  $R_1=R_3=H$, $R_2=F$, $R_4=CH_2CH_2CH_2CH_3$ Scheme 6 shows the synthesis of 2-(2,4,5-trimethoxyphenyl)-5-(3-hydroxyureidyl propoxy) tetrahydrofuran (13) and 2-(4-fluorophenyl)5-(3-hydroxyureidylprolpoxy)tetrahydrofuran (14,15)

Scheme 6

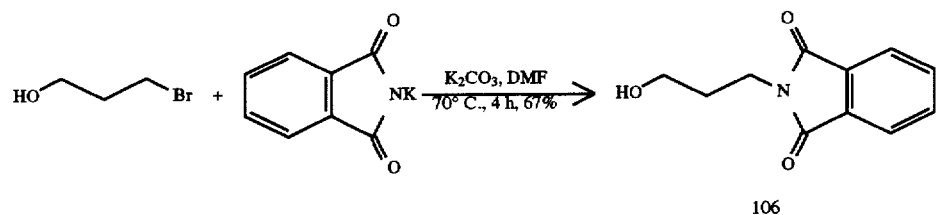

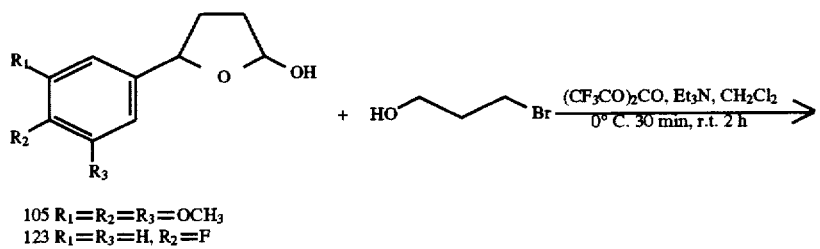

105 $R_1=R_2=R_3=OCH_3$
123 $R_1=R_3=H$, $R_2=F$

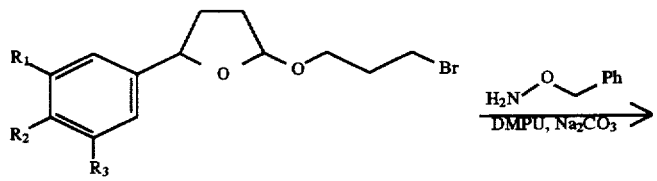

trans isomers: 128 $R_1=R_2=R_3=OCH_3$;
129 $R_1=R_3=H$, $R_2=F$
cis isomers: 130 $R_1=R_3=H$, $R_2=F$

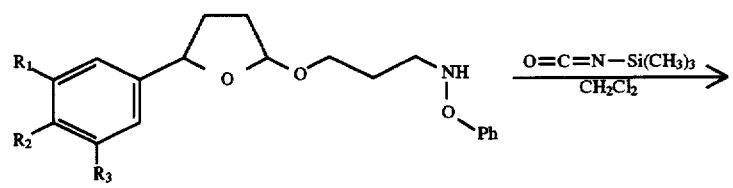

trans isomers: 131 $R_1=R_2=R_3=OCH_3$;
132 $R_1=R_3=H$, $R_2=F$
cis isomers: 133 $R_1=R_3=H$, $R_2=F$ -continued
Scheme 6
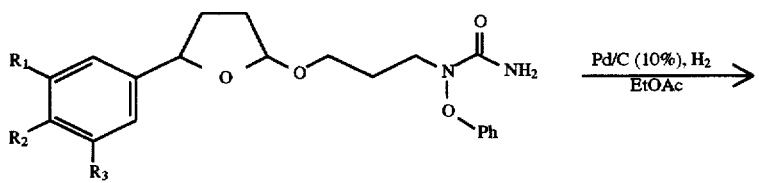
trans isomers: 134 $R_1=R_2=R_3=OCH_3$;
    135 $R_1=R_3=H, R_2=F$
cis isomers: 136 $R_1=R_3=H, R_2=F$
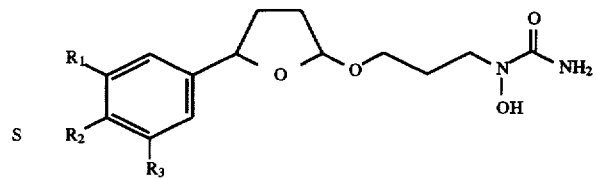
trans isomers: 13 $R_1=R_2=R_3=OCH_3$;
    14 $R_1=R_3=H, R_2=F$
cis isomers: 15 $R_1=R_3=H, R_2=F$
Scheme 7 shows the synthesis of 2-(3,4-dimethoxyphenyl)-5-[3-N'-substituted-N'-hydroxyureidyl propoxy]tetrahydrofuran (5–8):
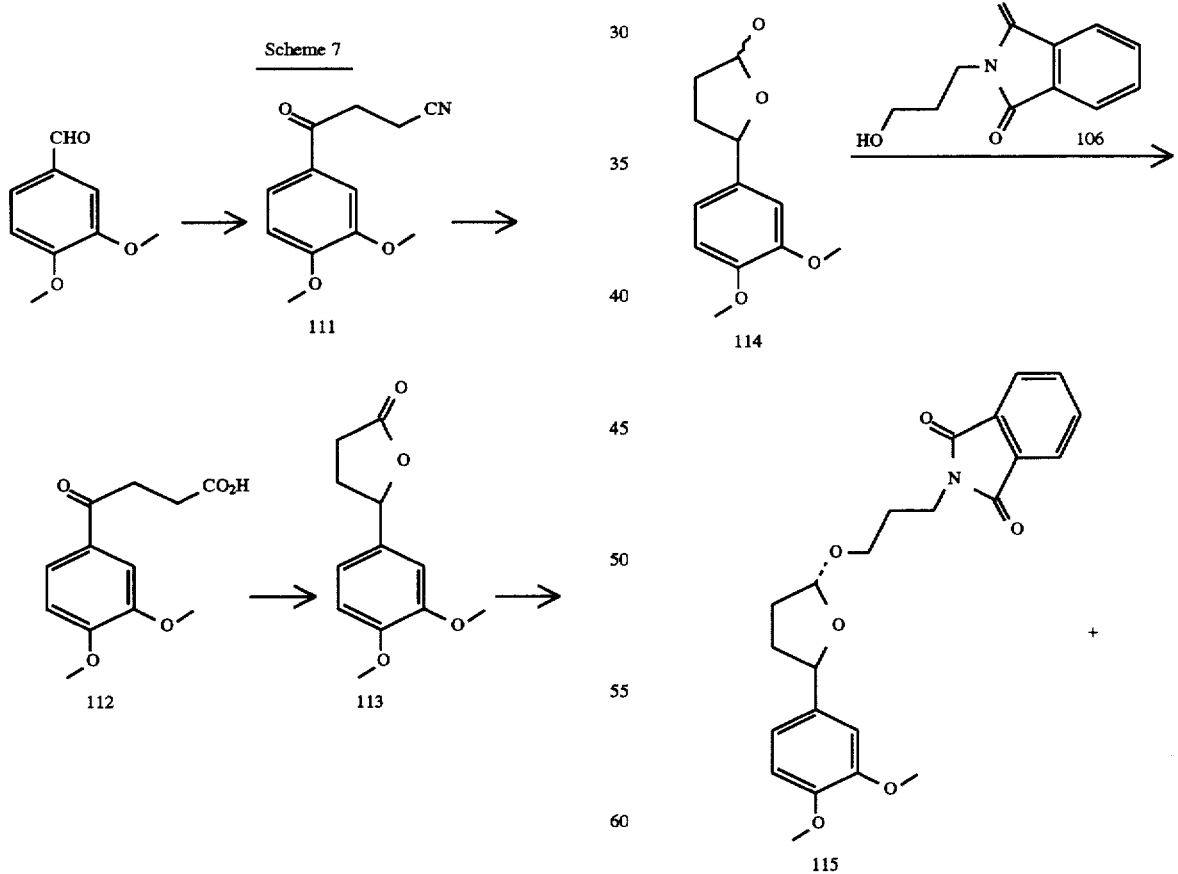

17
-continued
Scheme 7

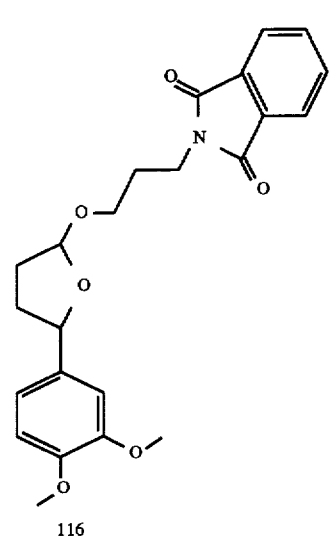

116

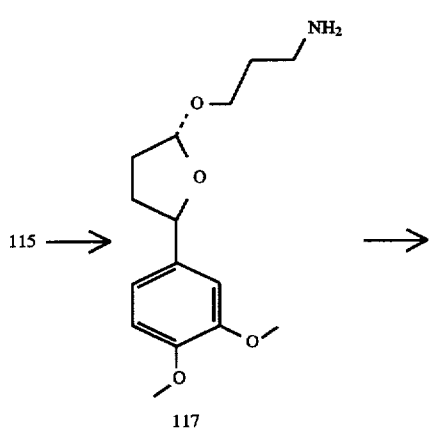

115 →

117

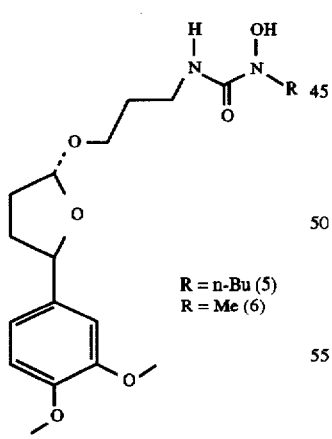

R = n-Bu (5)
R = Me (6)

18
-continued
Scheme 7

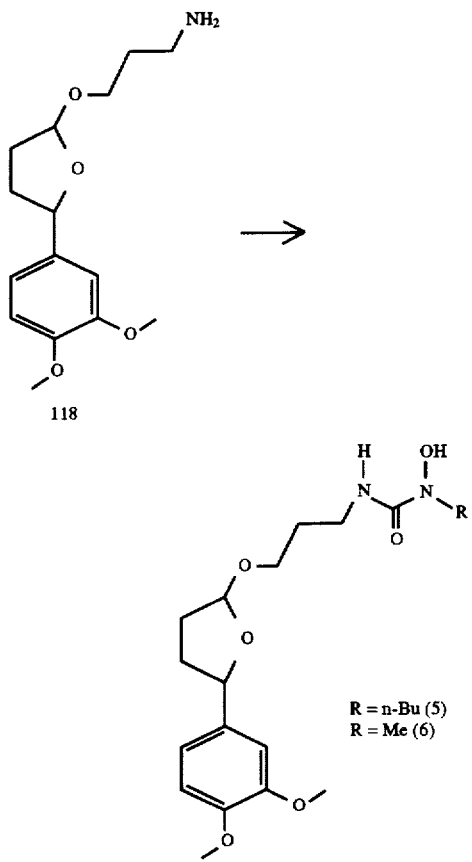

116 →

118

R = n-Bu (5)
R = Me (6)

The following examples are merely illustrative, and not intended to limit the scope of the invention.

EXAMPLE 1

Preparation of 2-(3,4,5-trimethoxyphenyl)-5-[3-(N'-substituted-N'-hydroxyureidyl)propoxy] tetrahydrofuran (1–4) and 2-(4-fluorophenyl)-5-[3-(N'-substituted-N'-hydroxyureidyl)propoxy] tetrahydrofuran (9–12)

(a) Preparation of 4-(3,4,5-trimethoxyphenyl)-4-ketone-butyric acid t-butyl ester (compound 101)

3,4,5-Trimethoxybenzaldehyde (8.0 g, 40.77 mmol), tert-butyl acrylate (5.29 g, 41.29 mmol) and the catalyst 3-ethyl-5-(2-hydroxyethyl)-4-methylthiazolium bromide (3.52 g, 13.95 mmol) were dissolved in 50 mL dimethyl formamide (DMF). To this solution was added 5.86 mL triethylamine. The reaction mixture was stirred at 60° C. for 16 hours, cooled to room temperature and quenched by adding 10% HCl (PH 1–2), and extracted with dichloromethane. The organic layer was washed with water and saturated NaCl solution, dried over MgSO$_4$, filtered and evaporated in vacuo to an oil. The product was purified by column chromatography (silica, 3:1 hexane/ethyl acetate) (4.5 g, 34%). $^1$H NMR (CDCl$_3$): 1.46(2,9H); 2.70(t,2H); 3.24(t, 2H); 3.92(s,9H); 7.25(s,2H).

(b) Preparation of 4-(4-fluorophenyl)-4-ketone-butyric acid t-butyl ester (compound 119)

This compound was prepared using a process similar to that set forth in Example 1(a), replacing the 3,4,5-trimethoxy-benzaldehyde with 4-fluorobenzaldehyde. $^1$H NMR (CDCl$_3$): 1.45(s,9H); 2.70(t,2H); 3.23(t,2H); 7.12(m, 2H); 8.02(m,2H)

(c) Preparation of 4-(3,4,5-trimethoxyphenyl)-4-hydroxy-butyric acid t-butyl ester (compound 102)

The ketone ester 101 (1.09 g, 3.36 mmol) was added to 10 mL THF and 20 mL methanol. An aqueous solution of NaBH$_4$ (127.3 mg, 3.36 mmol in 5 mL water) was added to this mixture in a dropwise manner at 0° C. The reaction mixture was stirred at room temperature for 4 hours, quenched with water and extracted with ethyl acetate. The organic layer was washed with water, saturated NaCl solution, dried over MgSO$_4$ filtered and evaporated in vacuo to provide the product (1.13 g, 103%). $^1$H NMR (CDCl$_3$): 1.46(s,9H); 2.02(m,2H); 2.37(t,2H); 3.84(s,3H); 3.88(s,6H); 4.70(m,1H); 6.58(s,2H).

(d) Preparation of 4-(4-fluorophenyl)-4-hydroxy-butyric acid t-butyl ester (compound 120)

This compound was prepared from 119 using a procedure similar to that set forth in Example 1(c), replacing compound 101 with compound 119. $^1$H NMR (CDCl$_3$): 1.44(s, 9H); 2.00(m,2H); 2.32(m,2H); 4.72(m,1H); 7.01(m,2H); 7.30(m,2H).

(e) Preparation of 4-(3,4,5-trimethoxyphenyl)-δ-lactone (compound 104)

The hydroxy ester 102 (1.13 g, 3.47 mmol) was added to 4 mL methanol, 1.5 mL water and 5M aqueous sodium hydroxide solution (4.5 mL). The reaction mixture was stirred at room temperature for 30 minutes and then 12 mL of saturated aqueous NaHCO$_3$ solution was added. The aqueous phase was washed with ether, acidified to pH 1–2 by adding conc. HCl, and extracted with benzene (2×30 mL). The benzene layer was checked by TLC which showed that some of the lactone has been formed. PPTS (10 mg) was added to the benzene extract and the mixture was refluxed for 1 hour to remove water. The reaction mixture was washed with saturated NaHCO$_3$ solution and evaporated in vacuo to provide the desired lactone as a solid (700 mg, 80%). $^1$H NMR (CDCl$_3$): 2.20(m,1H); 2.68(m,3H); 3.85(s, 3H); 3.88(s,6H); 5.46(m,1H); 6.55(s,2H).

(f) Preparation of 4-(4-fluorophenyl)-δ-lactone (compound 122)

This compound was prepared from 120 using a procedure similar to that set forth in Example 1(e), replacing compound 102 with compound 120. $^1$H NMR (CDCl$_3$): 2.20(m, 1H); 2.68(m,3H); 5.50(m,1H); 7.10(t,2H); 7.32(m,2H).

(g) Preparation of 2-(3,4,5-trimethoxyphenyl)-5-hydroxy-tetrahydrofuran (105)

Lactone 104 (6.86 g, 27.22 mmol) was dissolved in dry toluene (100 mL) and the solution was cooled to –70° C. A 1.5M toluene solution of DIBALH (28 mL) was added to the solution in a dropwise manner. The reaction mixture was stirred at –70° C. for 1 hour. The reaction was quenched through the addition of methanol (11 mL) while maintaining a temperature of <–60° C. The mixture was warmed to –20° C. followed by the addition of saturated aqueous potassium sodium tartrate solution (96 mL) while the reaction temperature was maintained between –10 and 0° C. The reaction mixture was stirred at 0° C. for 3 hours and then the two phases were separated. The aqueous layer was extracted with ethyl acetate. The combined organic layers were washed with water, saturated NaCl solution, and then concentrated in vacuo to afford the product (6.51 g, 94%). $^1$H NMR (CDCl$_3$): 1.82–2.48(m,4H); 3.84(s,3H); 3.88(s,6H); 4.97, 5.20(m,1H); 5.65, 5.79(m,1H); 6.56, 6.70(s,2H).

(h) Preparation of 2-(4-fluorophenyl)-5-hydroxy-tetrahydrofuran (123)

This compound was prepared from 122 using a procedure similar to that set forth in Example 1(g), replacing compound 104 with compound 122. $^1$H NMR (CDCl$_3$): 1.79(m, 1H); 1.95–2.10(m,1H); 2.20–2.32(m,1H); 2.48(m,1H); 5.00 & 5.22(m,1H); 5.63 & 5.78(m,1H); 7.04(m,2H); 7.30 & 7.41(m,2H).

(i) Preparation of trans and cis 2-(3,4,5-trimethoxyphenyl)-5-(3-phthalimidyl propoxy) tetrahydrofuran (compounds 107, 108)

Compound 105 (1.14 g, 4.49 mmol) was dissolved in 4 mL dichloromethane. Triethylamine (681.4 mg, 6.73 mmol) was added to this solution. The reaction mixture was cooled with an ice bath and trifluoroacetic anhydride (1.41 g, 6.73 mmol) was added in a dropwise manner. The reaction mixture was stirred at 0° C. for 30 minutes and then 3-phthalimidylpropanol (106) (2.4 g, 13.26 mmol) was added. The reaction mixture was warmed to room temperature and stirred at room temperature for 2 hours. The reaction was quenched with saturated aqueous NaHCO$_3$ solution and extracted with ethyl acetate. The organic layer was washed with water and saturated NaCl solution, dried over MgSO$_4$, filtered and evaporated in vacuo to an oil which was purified by column chromatography (silica, 2:1 hexane/ethyl acetate) (107: 522 mg (trans); 108: 271 mg (cis); 1:1 mixture of 107 and 108: 110 mg; total yield 46%). $^1$H NMR (CDCl$_3$): 107: 1.70(m,1H); 1.82(m,1H); 2.00(m, 2H); 2.02(m,1H); 2.28(m,1H); 3.46(m,1H); 3.83(s,3H); 3.84 (m,3H); 3.88(s,6H); 4.99(t,1H); 5.30(dd,1H); 6.56(s,2H); 7.72(m,2H); 7.85(m,2H). 108: 1.95(m,3H); 2.00(m,2H); 2.20(m,1H); 3.51(m,1H); 3.83(s,3H); 3.85(m,2H); 3.88(s, 6H); 3.92(m,1H); 4.90(m,1H); 5.16(dd,1H); 6.60(s,2H); 7.72(m,2H); 7.84(m,2H).

In order to determine the stereochemistry of this molecule, an NOE difference experiment was carried out.

Trans isomer (107): In this experiment the triplet at 4.99 ppm was irradiated with a very low rf decoupling pulse and the data work-up was done so as to only measure the presence of an increase in signal. This would represent a positive NOE effect and would indicate the close spacial relationship of these protons. In this experiment an NOE was found for the multiplet at 2.25–2.36 ppm which is a furan ring proton. Another NOE was also seen for the aromatic protons, indicating that this triplet represents the benzylic proton. There was not an NOE observed for the double doublet at 5.30 ppm indicating this was the trans isomer.

Cis isomer (108): In order to determine the stereochemistry of this molecule an NOE difference experiment was carried out. In this experiment the multiplet at 4.88–4.93 ppm was irradiated with a very low rf decoupling pulse and the data work-up was done so as to only measure the presence of an increase in signal. This would represent a positive NOE effect: and would indicate the close spacial relationship of these protons. In this experiment an NOE was found for the doublet at 5.16 ppm which is the other methine furan proton. Another NOE was also seen for the aromatic protons indicating this triplet represents the benzylic proton. There was also an NOE observed for the multiplet at 1.93–2.20 ppm for the other furan methylene protons.

(j) Preparation of 2-(4-Fluorophenyl)-5-(3-phthalimidyl propoxy) tetrahydrofuran (compounds 124, 125)

These compounds were prepared from 123 using a procedure similar to that set forth in Example 1(i), replacing compound 105 with compound 123. $^1$H NMR (CDCl$_3$): 124 (trans): 1.65(m,1H); 1.80(m,1H); 2.00(m,2H); 2.12(m,1H); 2.31(m,1H); 3.48(m,1H); 3.82(m,3H); 5.02(t,1H); 5.28(dd, 1H); 7.00(t,2H); 7.29(m,2H); 7.71(m,2H); 7.85(m,2H). 125 (cis): 1.90(m,2H); 1.99(m,4H); 2.19(m,1H); 3.48(m,1H); 3.82(m,2H); 3.88(m,1H); 4.94(m,1H); 5.15(dd,1H); 7.00(t, 2H); 7.30(m,2H); 7.71(m,2H); 7.84(m,2H).

(k) Preparation of 3-phthalimidylpropanol (compound 106)

3-Bromopropanol (4.0 g, 28.78 mmol), potassium phthalimide (8.0 g, 43.17 mmol) and potassium carbonate (4.0 g, 28.78 mmol) were added to 20 mL DMF. The reaction mixture was stirred at 70° C. for 4 hours, quenched with water and extracted with ethyl acetate. The organic layer was washed with water, saturated NaCl solution and evaporated in vacuo to a solid which was crystallized in ethyl acetate (3.5 g. 67%).

(l) Preparation of trans and cis 2-(3,4,5-trimethoxyphenyl)-5-(3-aminopropoxy)tetrahydrofuran (compounds 109, 110)

Compound 107 (455 mg, 1.03 mmol) and hydrazine monohydrate (165.3 mg, 5.16 mmol) were added to 2 mL ethanol. The reaction mixture was refluxed for 2 hours, quenched with water and extracted with dichloromethane. The organic layer was washed with water and saturated NaCl solution, dried over MgSO$_4$, filtered and evaporated in vacuo to provide the trans product 109 (225 mg, 70%). $^1$H NMR (CDCl$_3$): 1.75(m,2H); 1.78(m,1H); 1.96(m,1H); 2.20 (m,1H); 2.40(m,1H); 2.82(t,2H); 3.55(m,1H); 3.81(m,1H); 3.83(s,3H); 3.87(s,6H); 5.00(t,1H); 5.34(dd,1H); 6.56(s, 2H).

The cis isomer 110 was prepared from 108 using a procedure similar to that described for 109. $^1$H NMR (CDCl$_3$): 1.76(m,2H); 2.08(m,3H); 2.27(m,1H); 2.82(t,2H); 3.55(m,1H); 3.84(s,3H); 3.88(s,6H); 3.92(m,1H); 4.95(m, 1H); 5.20(m,1H); 6.64(s,2H).

(m) Preparation of 2-(4-fluorophenyl)-5-(3-aminopropoxy) tetrahydrofuran (compounds 126, 127)

These compounds were prepared from 124 and 125 using a procedure similar to that set forth in Example 1(l), replacing compounds 107 and 108 with compounds 124 and 125. $^1$H NMR (CDCl$_3$): 124 (trans): 1.75(m,3H); 1.96(m,1H); 2.20(m,1H); 2.40(m,1H); 2.82(t,2H); 3.54(m,1H); 3.83(m, 1H); 5.05(t,1H); 5.32(dd,1H); 7.01(t,2H); 7.30(m,2H). 125 (cis): 1.74(m,2H); 1.97(m,1H); 2.05(m,2H); 2.25(m,1H); 2.77(t,2H); 3.47(m,1H); 3.85(m,1H); 4.95(m,1H); 5.15(dd, 1H); 7.00(t,2H); 7.34(m,2H).

(n) Preparation of trans and cis 2-(3,4,5-trimethoxyphenyl)-5-[3-(N'-methyl-N'-hydroxyureidyl) propoxy]tetrahydrofuran (compounds 1, 3)

Compound 109 (60 mg, 0.19 mmol) and triphosgene (23 mg, 0.078 mmol) were dissolved in 3 mL dichloromethane. Triethylamine (29.3, 0.29 mmol) was added to this solution. The reaction mixture was refluxed for 2 hours and then cooled with ice bath. Triethylamine (34.0 mg, 0.34 mmol) and methylhydroxyamine hydrochloride (32.2 mg, 0.39 mmol) were added to the cold solution. The reaction was stirred at room temperature for 16 hours, quenched with water and extracted with dichloromethane. The organic layer was washed with saturated NaCl solution and evaporated in vacuo to an oil which was purified by preparative TLC (silica, ethyl acetate) to provide the trans product 1 (51 mg, 69%). $^1$H NMR (CDCl$_3$): 1.82(m,3H); 1.95(m,1H); 2.22(m, 1H); 2.40(m,1H); 3.15(s,3H); 3.40(m,2H); 3.58(m,1H); 3.84 (s,3H); 3.85(m,1H); 3.88(s,6H); 5.00(t,1H); 5.33(m,1H); 6.32(m,1H); 6.56(s,2H); 7.37(s,1H).

The cis isomer 3 was prepared from 110 using a procedure similar to that described for 1. $^1$H NMR (CDCl$_3$): 1.83(m, 2H); 2.07(m,3H); 2.28(m,1H); 3.13(s,3H); 3.35(m,2H); 3.55 (m,1H); 3.84(s,3H); 3.87(s,6H); 3.88(m,1H); 4.97(m,1H); 5.20(m,1H); 6.22(m,1H); 6.63(s,2H); 7.37(s,1H).

(o) Preparation of 2-(4-fluorophenyl)-5-[3-(N'-methyl-N'-hydroxyureidyl)propoxy]tetrahydrofuran (compounds 9, 11)

These compounds were prepared from 126 and 127 using a procedure similar to that set forth in Example 1(n) replacing compounds 109 and 110 with compounds 126 and 127. $^1$H NMR (CDCl$_3$): 9 (trans): 1.70(m,1H); 1.78(m,2H); 1.96 (m,1H); 2.19(m,1H); 2.40(m,1H); 3.10(s,3H); 3.31(m,2H); 3.51(m,1H); 3.83(m,1H); 5.05(t,1H); 5.30(dd,1H); 6.38(t, 1H); 7.01(t,2H); 7.28(m,2H). 11 (cis): 1.80(m,2H); 2.05(m, 3H); 2.24(m,1H); 3.06(s,3H); 3.30(m,2H); 3.48(m,1H); 3.86 (m,1H); 4.98(m,1); 5.16(dd,1H); 6.30(t,1H); 7.02(t,2H); 7.31(m,2H); 8.08(bs,1H)

(p) Preparation of trans and cis 2-(3,4,5-trimethoxyphenyl)-5[3-(N'-n-butyl-N'-hydroxyureidyl) propoxy]tetrahydrofuran (compounds 2,4)

Compound 109 (60 mg, 0.19 mmol) and triphosgene (23 mg, 0.078 mmol) were dissolved in 3 mL dichloromethane. Triethylamine (29.3, 0.29 mmol) was added to this solution. The reaction mixture was refluxed for 2 hours and then cooled with ice bath. Butylhydroxyamine (51.4 mg, 0.29 mmol) was added to the cold solution. The reaction mixture was stirred at room temperature for 16 hours, quenched with water and extracted with dichloromethane. The organic layer was washed with saturated NaCl solution and evaporated in vacuo to an oil. The trans product 2 was separated by preparative TLC (silica, ethyl acetate) (46.9 mg, 57%). $^1$H NMR (CDCl$_3$): 0.93(t,3H); 1.35(m,2H); 1.58(m,2H); 1.81 (m,3H); 1.96(m,1H); 2.21(m,1H); 2.40(m,1H); 3.38(m,2H); 3.50(m,2H); 3.57(m,1H); 3.83(s,3H); 3.85(m,1H); 3.88(s, 6H); 5.00(t,1H); 5.32(m,1H); 6.32(m,1H); 6.56(s,2H).

The cis isomer 4 was prepared from 110 using a procedure similar to that described for 2. $^1$H NMR (CDCl$_3$): 0.92(t, 3H); 1.32(m,2H); 1.58(m,2H); 1.81(m,2H); 2.08(m,3H); 2.28(m,1H); 3.35(m,2H); 3.47(m,2H); 3.54(m,1H); 3.84(s, 3H); 3.87(s,6H); 3.88(M,1H); 4.97(m,1H); 5.20(m,1H); 6.22(m,1H); 6.63(s,2H).

(q) Preparation of 2-(4-fluorophenyl)-5[3-(N'-n-butyl-N'-hydroxyureidyl)propoxy]tetrahydrofuran (compounds 10,12)

These compounds were prepared from 126 and 127 using a procedure similar to that set forth in Example 1(p) replacing compounds 109 and 110 with compounds 126 and 127. $^1$H NMR (CDCl$_3$): 10 (trans): 0.90(t,3H); 1.30(m,2H); 1.55 (m,2H); 1.70(m,1H); 1.78(m,2H); 1.96(m,1H); 2.19(m,1H); 2.40(m,1H); 3.31(m,2H); 3.44(m,2H); 3.52(m,1H); 3.82(m, 1H); 5.05(t,1H); 5.30(dd,1H); 6.32(t,1H); 7.00(t,2H); 7.28 (m,2H); 7.55(bs,1H). 12 (cis): 0.90(t,3H); 1.30(m,2H); 1.52 (m,2H); 1.80(m,2H); 2.04(m,3H); 2.24(m,1H); 3.30(m,2H); 3.40(m,2H); 3.48(m,1H); 3.85(m,1H); 4.98(t,1H); 5.16(dd, 1H); 6.27(t,1H); 7.03(t,2H); 7.32(m,2H); 7.53(bs,1H).

EXAMPLE 2

Preparation of 2-(3,4-Dimethoxyphenyl)-5-[3-N'-substituted-N'-hydroxyureidyl propoxy] tetrahydrofuran (5–8)

(a) Preparation of 4-(3',4'-dimethoxyphenyl)-4-oxobutyronitrile (111).

A single portion of neat acrylonitrile (3.2 ml, 0.048 mol) and triethylamine (5 ml, 0.11 mol) was added to a stirred mixture of 3,4-dimethoxybenzaldehyde (7.8 g, 0.047 mol) and 3-benzyl-5-(2-hydroxyethyl)-4-methylthiazolium chloride (5.3 g, 0.02 mol) in dry dimethylformamide (25 ml) under argon. The mixture was left overnight at room temperature. The reaction was diluted with water and extracted with ethyl acetate (3×100 ml). The organic extract was washed with water (3×100 ml), brine (3×100 ml) and the solvent was removed under reduced pressure to give an amber oil. Analysis by TLC (silica gel; ethyl acetate:hexanes, 1:1) revealed a mixture of three spots at Rf 0.80 (starting aldehyde), 0.50 (Compound 1) and 0.30 (unknown by-product). The sample was purified by column (flash) chromatography on silica gel 60 (230–400 mesh) and eluted with ethyl acetate:hexanes (1:1) to give the desired compound (2.26 g, 22%) as a yellow solid. $^1$H NMR (CDCl$_3$) 2.78 (t, 2H, J=8 Hz), 3.33 (t, 2H, J=8 Hz), 3.96 (s, 3H), 3.98 (s, 3H), 6.90(d, 1H, J=8.5 Hz), 7.52 (d, J=2 Hz, 2H), 7.58 (dd, J=2 and 8 Hz, 2H).

(b) Preparation of 4-(3',4'-dimethoxyphenyl)-4-oxobutyric acid (112).

A stirred solution of 4-(3',4'-dimethoxyphenyl)-4-oxobutyronitrile (111) (2.26 g, 0.01 mol) in acetic acid (15 ml) and hydrochloric acid (12N, 40 ml) was heated at reflux for 1.5 hours and cooled to room temperature. The solvent was removed under reduced pressure to give a brown solid. Recrystallization from water gave 112 as light tan crystals (1.57 g, 66%). $^1$H NMR (CDCl$_3$) 2.80 (t, J=7.5 Hz, 2H), 3.30 (t, J=7.5 Hz, 2H), 3.94 (s, 3H), 3.96 (s, 3H), 6.89 (d, 1H, J=9 Hz), 7.55 (d, 1H, J=1 Hz) and 7.64 (dd, 1H, 1 and 9 Hz).

(c) Preparation of 4-(3',4'-dimethoxyphenyl) butyrolactone (113).

A solution of sodium borohydride (0.89 g, 0.023 mol) in water (4 ml) was added dropwise (ca. 5 min) to a stirred solution of 112 (2.8 g, 0.012 mol) in dry, freshly distilled tetrahydrofuran (40 ml) and methanol (20 ml) under argon. The reaction was left overnight at room temperature. Analysis by TLC (silica gel; ethyl acetate:methanol:acetic acid, 9.5:0.5:few drops) indicated the presence of starting material. An additional charge of sodium borohydride (0.5 g, 0.013 mol) in water (2 ml) was added dropwise and the reaction left at room temperature for three hours. Analysis by TLC (same system as above) indicated the absence of starting material. The reaction was quenched with hydrochloric acid (6N, 25 ml) and left at room temperature for 15 minutes. The mixture was extracted with ethyl acetate (3×75 ml). The organic extract was washed with water (3×75 ml), brine (3×75 ml) and the solvent removed under reduced pressure to give a tan solid (2.0 g, 75%). $^1$H NMR (CDCl$_3$) 2.18–2.25 (m, 1H), 2.59–2.70 (m, 3H), 3.89 (s, 3H), 3.90 (s, 3H), 5.44–5.49 (m, 1H) and 6.82–6.87 (m, 3H).

(d) Preparation of 4-(3',4'-dimethoxyphenyl)butyrolactol (114).

A solution of diisobutylaluminum hydride (1.5M, 9 ml, 13.5 mmol) was added in a dropwise manner (ca. 30 min.) to 113 (2.0 g, 9 mmol) in dry toluene (40 ml) under argon which was cooled by a dry ice-acetone bath. The reaction was stirred at −78° C. for one hour. Analysis by TLC (silica gel; ethyl acetate:hexanes, 1:1) revealed the absence of starting material and the presence of a new spot at Rf 0.38. The reaction was quenched with methanol (20 ml) and slowly warmed to 0° C. A saturated solution of sodium potassium tartrate (50 ml) was added and stirred at 0° C. for 45 minutes. The mixture was extracted with ethyl acetate (3×100 ml) and the organic extract washed with water (3×75 ml) and brine (3×75 ml). Removal of the solvent under reduced pressure gave a dark amber oil (1.7 g, 84%). $^1$H NMR (CDCl$_3$) (mixture of cis and trans isomers) 1.71–2.49 (m, 8H), 2.91 (br s, 1H), 3.09 (br s, 1H), 3.89 (s, 6H), 3.90(s, 6H), 4.97 (m, 1H), 5.19 (t, J=7Hz, 1H), 5.62 (m, 1H), 5.77 (m, 1H) and 6.82–7.28 (m, 6H).

(e) Preparation of N-(3-hydroxypropyl)phthalimide (106).

A mixture of 3-bromopropanol (4 g, 0.029 mol), potassium phthalate (8 g, 0.043 mol) and potassium carbonate (4 g, 0.029 mol) in dry DMF (50 ml) was stirred and heated at 70° C. for four hours. The mixture was diluted with water (100 ml) and extracted with ethyl acetate (3×75 ml). The organic extract was washed with water (3×100 ml) and dried (Na$_2$SO4). Removal of the solvent under reduced pressure left a white solid which was extracted with benzene. The benzene extract was evaporated to a white solid and recrystallized from ethyl acetate-hexanes to give white crystals (1.27 g, 24%).

(f) Preparation of trans and cis 2-(3',4'-dimethoxyphenyl)-5-[3-(N-phthaloyl)]propoxytetrahydrofuran (115 and 116).

Triflic anhydride (0.68 ml, 4.8 mmol) was added in a single portion to a stirred solution of 114 (0.72 g, 3.2 mmol) in dry dichloromethane (20 ml) and triethylamine (0.68 ml, 4.9 mmol) under argon which was cooled using an ice bath. The reaction was stirred at 0° C. for 30 minutes. N-(3-hydroxypropyl)phthalimide (106) (1.27 g, 7 mmol) was added to the reaction mixture and the solution was allowed to warm to room temperature and left at this temperature for two hours. The solution was quenched with aqueous sodium bicarbonate solution (saturated, 25 ml) and extracted with ethyl acetate (3×50 ml), brine (3×50 ml) and dried (sodium sulfate). Removal of the solvent under reduced pressure left an amber oil (2.02 g). Analysis of the oil by TLC (silica gel; ethyl acetate:hexanes, 1:1) revealed the presence of four spots at Rf 0.80, 0.60, 0.50 and 0.35. The spots at Rf 0.60 and 0.50 were in a 2:1 ratio. The sample was purified by column chromatography (flash) on silica gel (230–400 mesh) and eluted with ethyl acetate:hexanes (3:7) to give first the substance at Rf 0.60 as a clear and colorless oil (0.40 g, 30%), identified as trans 2-(3',4'-dimethoxyphenyl)-5-[3-(N-phthaloyl)]-propoxytetrahydrofuran (115) (0.40 g, 30%). $^1$H NMR (CDCl$_3$) 1.34–1.94 (m, 2H), 1.96–2.05 (m, 2H), 2.09–2.20 (m, 1H), 2.25–2.36 (m, 1H), 3.46–3.53 (m, 1H), 3.84 (t, 9 Hz, 2H), there is also a hidden 1 proton multiplet here, 3.88 (s, 3H), 3.91 (s, 3H), 5.01 (t, 7.3Hz, 1H), 5.30 (dd, J=2 and 5 Hz, 1 Hz), 6.82–6.90 (m, 3H), 7.71–7.74 (m, 2H) and 7.84–7.88 (m, 2H).

In order to determine the stereochemistry of this molecule and NOE difference experiment was carried out. In this experiment the triplet at 5.01 ppm was irradiated with a very low rf decoupling pulse and the data work-up was done so as to only measure the presence of an increase in signal. This would represent a positive NOE effect and would indicate the close spatial relationship of these protons. In this experiment an NOE was found for the multiplet at 2.25–2.36 ppm which is a furan ring proton. Another NOE was also seen for the aromatic protons indicating this triplet presents the benzylic proton. There was not an NOE observed for the double doublet at 5.30 ppm indicating this was the trans isomer.

Continued elution with the same solvent system gave the spot at Rf 0.50 as a colorless oil (0.21 g, 15%), identified as cis 2-(3',4'-dimethoxyphenyl)-5-[3-(N-phthaloyl)]propoxytetrahydrofuran (116). $^1$H NMR (CDCl$_3$) 1.92–2.12 (m, 6H), 3.44–3.52 (m, 1H), 3.86 (s, 3H), 3.88 (s, 3H), 3.76–3.93 (m, 3H), 4.89–4.94 (m, 1H), 5.35 (d, J=4 Hz), 6.89 (d, J=8 Hz), 6.87 (dd, J=2 and 8 Hz), 6.92 (d, J=2 Hz), 7.69–7.72 (m, 2H) and 7.82–7.85 (m, 2H).

In order to determine the stereochemistry of this molecule an NOE difference experiment was carried out. In this experiment the multiplet at 4.89–4.94 ppm was irradiated with a very low rf decoupling pulse and the data work-up was done so as to only measure the presence of an increase in signal. This would represent a positive NOE effect and would indicate the close spatial relationship of these protons. In this experiment an NOE was found for the doublet at 5.35 ppm which is the other methine furan proton. This indicates that this molecule is the cis isomer. Another NOE was also seen for the aromatic protons indicating this triplet presents the benzylic proton. There was also an NOE present for the multiplet at 1.92–2.12 ppm which contains the other furan methylene protons.

The chromatography also yielded a mixture of 115 and 116 (0.342 g, 26%).

(g) Preparation of trans 2-(3',4'-dimethoxyphenyl)-5-(3-aminopropoxy)tetrahydrofuran (117).

Neat hydrazine hydrate (150 μl, 3.2 mmol) was added to a stirred solution of 115 (253 mg, 0.62 mmol) in absolute ethanol (1.5 ml). The solution was heated at reflux for 5 minutes whereupon a white solid precipitated out of solution. The mixture was heated at reflux for two hours. Analysis by TLC (silica gel; ethyl acetate:hexanes, 1:1) revealed the absence of starting material and the presence of a spot at the origin. The reaction was quenched with water (10 ml) and extracted with dichloromethane (5×10 ml). The organic phase was washed with water (2×10 ml), brine (2×10 ml) and dried (sodium sulfate). Removal of the solvent under reduced pressure left a colorless oil (150 mg, 86%). $^1$H NMR (CDCl$_3$) 1.25 (br s, 2H), 1.68–1.78 (m, 3H), 1.81–1.98 (m, 1H), 2.14–2.2 (m, 1H), 2.3–2.36 (m, 1H), 2.80 (t, J=6.5 Hz, 2H), 3.47–3.55 (m, 1H), 3.78–3.87 (m, partially hidden, 1H), 3.86 (s, 3H), 3.88 (s, 3H), 4.99 (t, J=7 Hz, 1H), 5.31 (dd, J=2 and 6 Hz, 1H), 6.80–6.88 (m, 3H).

(h) Preparation of cis 2-(3',4'-dimethoxyphenyl)-5-(3-aminopropoxy)tetrahydrofuran (118).

Neat hydrazine hydrate (125 μl, 2.57 mmol) was added to a stirred solution of 116 (210 mg, 0.51 mmol) in absolute ethanol (3.0 ml). The solution was heated at ref lux for 5 minutes whereupon a white solid precipitated out of solution. The mixture was heated at reflux for two hours. Analysis by TLC (silica gel; ethyl acetate:hexanes, 1:1) revealed the absence of starting material and the presence of a spot at the origin. The reaction was quenched with water (10 ml) and extracted with dichloromethane (5×10 ml). The organic phase was washed with water (2×10 ml), brine (1×10 ml) and dried (sodium sulfate). Removal of the solvent under reduced pressure left a stiff oil (105 mg, 73%). $^1$H NMR (CDCl$_3$) 1.45 (br s, 2H), 1.73–1.78 (m, 2H), 2.01–2.12 (m, 3H), 2.19–2.29 (m, 1H), 2.81 (t, J=7 Hz, 2H), 3.48–3.53 (m, 1H), 3.85–3.93 (m, partially hidden, 1H), 3.88 (s, 3H), 3.90 (s, 3H), 4.96–5.01 (m, 1H), 5.17 (dd, J=3 and 6 Hz, 1H), 6.83 (d, J=8 Hz, 1H), 6.89 (dd, J=2 and 8 Hz, 1H) and 6.96 (d, J=2 Hz, 1H).

(i) Preparation of trans 2-(3',4'-dimethoxyphenyl)-5-[3-(N-butyl-N-hydroxyureidyl)propoxy]tetrahydrofuran (5).

Triethylamine (32 μl, 0.22 mmol) and then triphosgene (19 mg, 0.06 mmol) were added to a stirred solution of 117 (53 mg, 0.19 mmol) in dry dichloromethane (3 ml) under argon. The solution was heated at reflux for 30 minutes and cooled to room temperature. Solid n-butylhydroxylamine (34 mg, 0.38 mmol) was added in one portion to the solution which was left overnight at room temperature. The reaction was quenched with water (10 ml) and extracted with dichloromethane (3×10 ml). The combined organic phase was washed with aqueous sodium bicarbonate solution (saturated, 3×10 ml) and dried (sodium sulfate). Analysis by TLC (silica gel, ethyl acetate) revealed a complex mixture Rf 0.90, 0.50, 0.25 and 0.00. The sample was purified by column (flash) chromatography on silica gel 60 (230–400 mesh) and eluted with ethyl acetate to give the spot at Rf 0.50 as an opaque oil (8 mg, 11%). $^1$H NMR (CDCl$_3$) 0.92 (t, J=7 Hz, 3H), 1.27–1.39 (m, 2H), 1.51–1.61 (m, 2H), 1.71–1.86 (m, 3H), 1.88–2.15 (m, 1H), 2.17–2.29 (m, 1H), 2.32–2.42 (m, 1H), 3.28–3.58 (m, 4H), 3.81–3.94 (m, partially hidden, 2H), 3.87 (s, 3H), 3.90 (s, 3H), 5.49–5.05 (m, 1H), 5.31–5.38 (m, 1H), 6.28–6.34 (m, 1H) and 6.81–6.86 (m, 3H). IR (film) 3407, 3193, 2933, 1640, 1516, 1263, 1029 cm$^{-1}$ (j) Preparation of trans 2-(3',4'-dimethoxyphenyl)-5-[3-(N-methyl-N-hydroxyureidyl)propoxy]tetrahydrofuran (6).

Triphosgene (12 mg, 0.04 mmol), followed immediately by triethylamine (17 μl, 0.12 mmol) was added to a stirred solution of 117 (32 mg, 0.011 mmol) in dry dichloroinethane (3 ml) under argon. The solution was heated at reflux for 2 hours, cooled to room temperature and placed in an ice bath. Neat triethylamine (32 μl, 0.23 mmol) followed by methylhydroxylamine hydrochloride salt (19 mg, 0.23 mmol) was added to the reaction mixture. The reaction was left overnight at room temperature. It was then quenched with water (10 ml) and extracted with dichloromethane (3×10 ml). The organic extract was washed with water (3×10 ml), brine (3×10 ml) and the solvent was removed under reduced pressure to give an amber oil. Analysis by TLC (silica gel, ethyl acetate) revealed only one new spot at Rf 0.30. The sample was purified by column (flash) chromatography on silica gel 60 (230–400 mesh) and eluted with ethyl acetate to give the desired compound as an amber oil (12 mg, 30%). $^1$H NMR (CDCl$_3$) 1.73–1.84 (m, 2H), 1.90–2.01 (m, 1H), 2.03–2.13 (m, 1H), 2.18–2.29 (m, 1H), 2.32–2.43 (m, 1H), 3.13 (s, 3H), 3.30–3.44 (m, 2H), 3.49–3.59 (m, 1H), 3.82–3.92 (m, partially hidden, 3H), 3.88 (s, 3H), 3.91 (m, 3H), 4.96–5.04 (m, 1H), 5.34 (dd, J=2 and 5 Hz, 1H), 6.34 (br t, 5 Hz, 1H) and 6.82–6.68 (m, 3H). IR (film) 3407, 3229, 2935, 1636, 1516, 1263 and 1029 cm$^{-1}$.

(k) Preparation of cis 2-(3',4'-dimethoxyphenyl)-5-[3-(N-butyl-N-hydroxyureidyl)propoxy]-tetrahydrofuran (7).

Triphosgene (18 mg, 0.06 mmol), followed immediately by triethylamine (80 μl, 0.57 mmol) were added to a stirred solution of 118 (50 mg, 0.18 mmol) in dry dichloromethane (3 ml) under argon. The solution was heated at reflux for 2 hours, cooled to room temperature and placed in an ice bath. Neat triethylamine (50 μl, 0.35 mmol) was added, followed by solid n-butylhydroxylamine (32 mg, 0.36 mmol). The reaction was left overnight at room temperature. It was then quenched with water (10 ml) and extracted with dichloromethane (3×10 ml). The organic extract was washed with water (3×10 ml), brine (3×10 ml), and the solvent was removed under reduced pressure to give an amber oil. Analysis by TLC (silica gel, ethyl acetate) revealed two new spots in approximately equal amounts at Rf 0.85 and 0.45. The sample was purified by column (flash) chromatography on silica gel 60 (230–400 mesh) and eluted with ethyl acetate to give first the spot at Rf 0.85 as an amber oil (26 mg). Continued elution with the same solvent system then gave the title compound as an amber oil (25 mg, 35%). $^1$H NMR (CDCl$_3$) 1.1 (t, J=7 Hz, 3H), 1.25–1.37 (m, 2H), 1.49–1.59 (m, 2H), 1.76–1.84 (m, 2H), 1.99–2.1 (m, 3H), 2.19–2.26 (m, 1H), 3.26–3.54 (m, 5H), 3.84–3.92 (m, partially hidden, 1H), 3.87 (s, 3H), 3.88 (s, 3H), 4.94–5.02 (m, 1H), 5.17 (d, J=4 Hz, 1H), 6.24 (t, J=4 Hz, 1H), 6.52 (br s, 1H), 6.83 (d, J=8 Hz, 1H) and 6.89–95 (m, 2H). IR (film) 2913, 1640, 1570, 1463, 1262, 1139 and 1031 cm$^{-1}$.

(l) Preparation of cis 2-(3',4'-dimethoxyphenyl)-5-[3-(N-methyl-N-hydroxyureidyl)propoxy]tetrahydrofuran (8).

Triphosgene (20 mg, 0.07 mmol), followed immediately by triethylamine (80 μl, 0.57 mmol)were added to a stirred solution of 118 (56 mg, 0.2 mmol) in dry dichloromethane (3 ml) under argon. The solution was heated at reflux for 2 hours, cooled to room temperature and placed in an ice bath. Neat triethylamine (80 μl, 0.57 mmol) was added followed by solid methyl hydroxylamine hydrochloride salt (32 mg, 0.39 mmol). The reaction was left overnight at room temperature. It was then quenched with water (10 ml) and extracted with dichloromethane (3×10 ml). The organic extract was washed with water (3×10 ml), brine (3×10 ml), and the solvent was removed under reduced pressure to give an amber oil. Analysis by TLC (silica gel, ethyl acetate) revealed one spot at rf 0.30 and some material at the origin. The sample was purified by column (flash) chromatography on silica gel 60 (230–400 mesh) and eluted with ethyl acetate to give the title compound as an amber oil (30 mg, 42%). $^1$H NMR (CDCl$_3$) 1.76 (m, 2H), 1.98–2.10 (m, 3H), 2.18–2.26 (m, 1H), 3.07 (s, 3H), 3.25–3.37 (m, 2H), 3.46–3.54 (m, 1H), 3.85–3.90 (m, partially hidden, 1H), 3.87 (s, 3H), 3.88 (s, 3H), 4.93–5.00 (m, 1H), 5.16 (d, J=4 Hz, 1H), 6.27 (t, J=5 Hz, 1H), 6.83 (d, J=8 Hz, 1H) and 6.88–6.93 (m, 2H). IR (neat) 2933, 1643, 1518, 1261 and 1029 cm$^{-1}$.

EXAMPLE 3

Preparation of 2-(2,4,5-trimethoxyphenyl)-5-(3-hydroxyureidyl propoxy)tetrahydrofuran (13) and 2-(4-fluorophenyl)5-(3-hydroxyureidylpropoxy)tetrahydrofuran (14, 15)

(a) Preparation of 2-(3,4,5-trimethoxyphenyl)-5-(3-bromopropoxy) tetrahydrofuran (compound 128)

Compound 105 (1.0 g, 3.94 mmol) was dissolved in 4 mL dichloromethane. Triethylamine (597 mg, 5.90 mmol) was added to this solution. The reaction mixture was cooled with an ice bath and trifluoroacetic anhydride (1.24 g, 5.90 mmol) was added dropwise. The reaction mixture was stirred at 0° C. for 30 minutes and then 3-bromopropanol (1.84 g, 13.27 mmol) was added. The reaction mixture was warmed to room temperature and stirred at room temperature for 2 hours. The reaction was quenched with saturated aqueous NaHCO$_3$ solution and extracted with ethyl acetate. The organic layer was washed with water and saturated NaCl solution, dried over MgSO$_4$, filtered and evaporated in vacuo to an oil which was purified by column chromatography (silica, 4:1 hexane/ethyl acetate) (128: 430 mg and its cis isomer 250 mg; total yield 46%). $^1$H NMR (CDCl$_3$): 128 (trans): 1.77(m,1H); 1.98(m,1H); 2.15(m,2H); 2.20(m,1H); 2.40(m,1H); 3.53(t,2H); 3.60(m,1H); 3.83(s,3H); 3.87(m, 1H); 3.89(s,6H); 5.01(t,1H); 5.35(dd,1H); 6.57(s,2H).

(b) Preparation of 2-(4-fluorophenyl)-5-(3-bromopropoxy) tetrahydrofuran (compounds 129, 130)

These compounds were prepared from 123 using a procedure similar to that set forth in Example 3(a), replacing compound 105 with compound 123. $^1$H NMR (CDCl$_3$): 129 (trans): 1.72(m,1H); 1.98(m,1H); 2.14(m,2H); 2.20(m,1H); 2.40(m,1H); 3.53(t,2H); 3.60(m,1H); 3.89(m,1H); 5.06(t, 1H); 5.34(m,1H); 7.02(t,2H); 7.30(m,2H). 130 (cis): 1.98 (m,1H); 2.07(m,2H); 2.14(m,2H); 2.26(m,1H); 3.52(t,2H); 3.58(m,1H); 3.93(m,1H); 5.00(m,1H); 5.20(dd,1H); 7.03(t, 2H); 7.35(m,2H).

(c) Preparation of 2-(3,4,5-trimethoxyphenyl)-5-(3-O-benzylhydroxylaminopropoxy)tetrahydrofuran (compounds 131)

Compound 128 (260 mg, 0.69 mmol) was dissolved in 2 mL 1,3-dimethyl-3,4,5,6-tetrahydro-2-(1H)-pyrimidinone (DMPU). Sodium carbonate (220.4 mg, 2.08 mmol) and benzylhydroxylamine hydrochloride (166 mg, 1.04 mmol) were added to this solution. The reaction was stirred at 80° C. for 16 hours, quenched with water and extracted with ethyl acetate. The organic layer was washed with water and saturated sodium chloride solution, dried over MgSO$_4$, filtered and evaporated to an oil which was purified by column (flash) chromatography using ethyl acetate as a solvent (114 mg, 40%). $^1$H NMR (CDCl$_3$): 1.72(m,1H); 1.82(m,2H); 1.92(m,1H); 2.18(m,1H); 2.36(m,1H); 3.06(t, 2H); 3.52(m,1H); 3.81(m,1H); 3.83(s,3H); 3.87(s,6H); 4.71 (s,2H); 4.98(t,1H); 5.30(dd,1H); 6.55(s,2H); 7.35(m,5H).

(d) Preparation of 2-(4-fluorophenyl)-5-(3-O-benzylhydroxylaminopropoxy)tetrahydrofuran (compounds 132,133)

These compounds were prepared from compounds 129 and 130 using a procedure similar to that set forth in Example 3(c), replacing compound 128 with compounds 129 and 130. $^1$H NMR (CDCl$_3$): 132 (trans): 1.70(m,1H); 1.83(m,2H); 1.94(m,1H); 2.17(m,1H); 2.38(m,1H); 3.07(t, 2H); 3.52(m,1H); 3.82(m,2H); 4.71(s,2H); 5.02(t,1H); 5.30 (ss,1H); 7.02(t,2H); 7.30(m,2H); 7.36(m,5H). 133 (cis): 1.85(m,2H); 1.96(m,1H); 2.05(m,2H); 2.26(m,1H); 3.05(t, 2H); 3.50(m,1H); 3.88(m,2H); 4.70(s,2H); 4.99(m,1H); 5.17 (dd,1H); 5.50(bs,1H); 7.00(t,2H); 7.35(m,7H)

(e) Preparation of 2-(3,4,5-trimethoxyphenyl)-5-(3-O-benzylhydroxyureidylpropoxy)tetrahydrofuran (compounds 134)

Compound 131 (114 mg, 0.27 mmol) was dissolved in 3 mL dichloromethane. Trimethylsilyl isocyanate (47.6 mg, 0.41 mmol) was added to this solution. The reaction was stirred at room temperature for 16 hours and then refluxed for 4 hours. The reaction was quenched with saturated ammonium chloride solution, extracted with ethyl acetate and evaporated to an oil. The product was isolated by preparative TLC using ethyl acetate as solvent. $^1$H NMR (CDCl$_3$): 1.72(m,1H); 1.94(m,3H); 2.16(m,1H); 2.38(m, 1H); 3.50(m,1H); 3.62(m,2H); 3.80(m,1H); 3.82(s,3H); 3.84 (s,6H); 4.81(s,2H); 4.99(t,1H); 5.30(m,3H); 6.54(s,2H); 7.37(s,5H).

(f) Preparation of 2-(4-fluorophenyl)-5-(3-O-benzylhydroxyureidylpropoxy)tetrahydrofuran (compounds 135, 136)

These compounds were prepared from 132 and 133 using a procedure similar to that set forth in Example 3(e), replacing compounds 131 with compounds 132 and 133. $^1$H NMR (CDCl$_3$): 135 (trans): 1.70(m,1H); 1.93(m,3H); 2.16 (m,1H); 2.39(m,1H); 3.50(m,1H); 3.62(m,2H); 3.80(m,1H); 4.82(s,2H); 5.04(t,1H); 5.30(dd,1H); 5.35(bs,2H); 7.00(t, 2H); 7.29(m,2H); 7.38(s,5H). 136 (cis): 1.98(m,4H); 2.08 (m,1H); 2.25(m,1H); 3.48(m,1H); 3.62(m,2H); 3.83(m,1H); 4.81(s,2H); 4.98(m,1H); 5.17(dd,1H); 5.42(bs,1H); 7.00(t, 2H); 7.33(m,2H); 7.38(s,5H).

(g) Preparation of 2-(3,4,5-trimethoxyphenyl)-5-(3-hydroxyureidylpropoxy)tetrahydrofuran (compounds 13)

Compound 134 (90 mg, 0.19 mmol) was dissolved in 2 mL ethyl acetate and then Pd/C (10%) (18 mg) was added. The reaction mixture was hydrogenated at balloon pressure for 16 hours. The reaction was filtered and the filtrate was concentrated. The product was isolated by preparative TLC using ethyl acetate as solvent (68 mg). $^1$H NMR (CDCl$_3$): 1.75(m,1H); 1.91(m,2H); 1.95(m,1H); 2.20(m,1H); 2.37(m, 1H); 3.58(m,1H); 3.66(m,2H); 3.81(s,3H); 3.85(m,1H); 3.87 (m,6H); 5.00(t,1H); 5.35(dd,1H); 5.41(bs,2H); 6.53(s,2H); 8.39(s,1H).

(h) Preparation of 2-(4-fluorophenyl)-5-(3-hydroxyureidylpropoxy)tetrahydrofuran (compounds 14, 15)

Compounds 14 and 15 were prepared from 135 and 136 using a procedure similar to that set forth in Example 3(g), replacing compound 134 with compounds 135 and 136. $^1$H NMR (CDCl$_3$): 14 (trans): 1.72(m,1H); 1.93(m,3H); 2.20 (m,1H); 2.38(m,1H); 3.58(m,1H); 3.67(m,2H); 3.85(m,1H); 5.05(t,1H); 5.33(dd,1H); 5.48(bs,2H); 7.00(t,2H); 7.28(m, 2H); 8.48(bs,1H). 15 (cis): 1.92(m,2H); 2.01(m,1H); 2.10 (m,2H); 2.26(m,1H); 3.53(m,1H); 3.64(m,2H); 3.87(m,1H); 4.98(m,1H); 5.20(dd,1H); 5.43(bs,2H); 7.01(m,2H); 7.31 (m,2H); 8.43(bs,1H).

II. Pharmaceutical Compositions

Humans, equines, canines, bovines and other animals, and in particular, mammals, suffering from inflammatory diseases, and in particular, disorders mediated by PAF or products of 5-lipoxygenase can be treated by administering to the patient an effective amount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, or topically, in liquid, cream, gel, or solid form, or by aerosol form.

As used herein, the term pharmaceutically acceptable salts or complexes refers to salts or complexes that retain the desired biological activity of the above-identified compounds and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. The compounds can also be administered as pharmaceutically acceptable quaternary salts known by those skilled in the art, which specifically include the quaternary ammonium salt of the formula —NR$^+$Z$^-$, wherein R is alkyl or benzyl, and Z is a counterion, including chloride, bromide, iodide, -O-alkyl, toluenesulfonate, methylsulfonate, sulfonate, phosphate, or carboxylate (such as benzoate, succinate, acetate, glycolate, maleate, malate, citrate, tart:rate, ascorbate, benzoate, cinnamoate, mandeloate, benzyloate, and diphenylacetate.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 10 ng/kg to 300 mg/kg, preferably 0.1 to 100 mg/kg per day, more generally 0.5 to about 25 mg per kilogram body weight of the recipient per day. A preferred dosage for cardiovascular indications is in the range 10 ng/kg to 20 mg/kg. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. A oral dosage of 25–250 mg is usually convenient.

The active ingredient is preferably administered to achieve peak plasma concentrations of the active compound of about 0.00001–30 mM, preferably about 0.1–30 µM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, othe Solunflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (CA) and Scios Nova (Baltimore, Md.).

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

III. Biological Activity

A wide variety of biological assays have been used to evaluate the ability of a compound to act as a PAF receptor antagonist, including the ability of the compound to bind to PAF receptors, and the effect of the compound on various PAF mediated pathways. Any of these known assays can be used to evaluate the ability of the compounds disclosed herein to act as PAF receptor antagonists.

For example, PAF is known to induce hemoconcentration and increased permeability of microcirculation leading to a decrease in plasma volume. PAF mediated acute circulatory collapse can be used as the basis of an assay to evaluate the ability of a compound to act as a PAF antagonist, by analyzing the effect of the compound on PAF induced decreased plasma volume in an animal model such as mouse.

Endotoxemia causes the release of chemical mediators including eicosanoids, PAF, and tumor necrosis factor (TNF) that stimulate a variety of physiologic responses including fever, hypotension, leukocytosis, and disturbances in glucose and lipid metabolism. Endotoxemia can result in severe shock and death. Endotoxin-induced mouse mortality is a useful animal model to evaluate the pharmacological effect of compounds on endotoxic shock.

Two other common assays used to evaluate the ability of a compound to act as a PAF receptor antagonist are platelet aggregation in vitro and hypotension in rats (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987)).

A wide variety of biological assays have also been used to evaluate the ability of a compound to inhibit the enzyme 5-lipoxygenase. For example, a cytosol 5-lipoxygenase of rat basophilic leukemia cells (RBL) has been widely utilized in studies on leukotriene biosynthesis. Compounds that inhibit 5-lipoxygenase decrease the levels of leukotrienes.

Another biological assay used to evaluate the ability of a compound to inhibit the enzyme 5-lipoxygenase is based on the classic pharmacological model of inflammation induced by inhibition of $LTB_4$ from ionophore stimulated human whole blood.

EXAMPLE 4

Ability of Compound to Bind to PAF Receptors (a) Preparation of Human Platelet Membranes Human platelet membranes are prepared from platelet concentrates obtained from the American Red Cross Blood Services (Dedham, Mass.). After several washes with platelet wash solution (150 mM NaCl, 10 mM Tris, and 2 mM EDTA, pH 7.5), the platelet pellets are resuspended in 5 mM $MgCl_2$, 10 mM Tris, and 2 mM EDTA at pH 7.0. The cells are then quickly frozen with liquid nitrogen and thawed slowly at room temperature. The freezing and thawing procedure is repeated at least three times. For further fractionation of membrane fragments, the lysed membrane suspension is layered over the top of a discontinuous sucrose density gradient of 0.25, 1.03, and 1.5M sucrose prepared in 10 mM $MgCl_2$, 10 mM Tris and 2 mM EDTA, pH 7.0, and centrifuged at 63,500×g for 2 hr. The membrane fractions banding between 0.25 and 1.03M (membrane A) and between 1.03 and 1.5M (membrane B) are collected separately. The protein concentration of the membrane preparations is determined by Lowry's method with bovine serum albumin (BSA) as the standard. The membranes are then separated into smaller fractions (4 ml each) and stored at −80° C. and thawed before use.

(b) [$^3$H]PAF Binding inhibition

The ability of [$^3$H]PAF to bind to specific receptors on human platelet membranes is evaluated at optimal conditions at pH 7.0 and in the presence of 10 mM $MgCl_2$. Membrane protein (100 µg) is added to a final 0.5 ml solution containing 0.15 pmol (0.3 nM concentration) of [$^3$H]PAF and a known amount of unlabeled PAF or PAF receptor antagonist in 10 mM $MgCl_2$, 10 mM Tris and 0.25% BSA at pH 7.0. After incubation for four hours at 0° C., the bound and unbound [$^3$H]PAF are separated through a Whatman GF/C glass fiber filter under vacuum. No degradation of filter bound [$^3$H]PAF should be detected under this assay condition. The nonspecific binding is defined as the total binding in the presence of excess unlabeled PAF (1 mM) where no further displacement is found with higher concentrations of either unlabeled PAF or PAF analogs or PAF receptor antagonists. The specific binding is defined as the difference between total binding and nonspecific binding.

To determine the relative potency of tested compounds, [³H]PAF binding in the presence of inhibitors is normalized in terms of percent inhibition by assigning the total binding in the absence of inhibitors as 0% inhibition and the total binding in the presence of 1 mM unlabeled PAF as 100%. The percent inhibition by the compound can be calculated by the formula expressed below:

% inhibition=[(Total binding–total binding in the presence of compound)/nonspecific binding]×100%

The $IC_{50}$ is calculated as the concentration of the inhibitor necessary to obtain 50% inhibition of the specific [³H]PAF binding and is calculated by a nonlinear regression computer software program. GraphPad Inplot:, version 3.0 (GraphPad software, San Diego, Calif.).

EXAMPLE 5

Effect of Compound on PAF-induced Hemoconcentration (a) Animals

Female CD-1 mice, weighing 16–20 grams, are obtained from Charles River Laboratory (Wilmington, Mass.). Tap water and rodent laboratory chow (5001, Purina Mills, St. Louis, Mo.) are provided ad libitum. The mice are housed for an average of four days prior to use.

(b) Hematocrit measurement

PAF (1-O-alkyl-2-acetyl-sn-glyceryl-3-phosphorylcholine, Sigma Chemical Co.) is dissolved in 0.25% bovine serum albumin (BSA) in 0.9% NaCl solution. Except for dose-response studies, 10 µg (10 ml/kg) of PAF solution is injected into the tail vein. All test compounds are dissolved in 0.5 DMSO saline solution and intravenously injected at 3 mg/kg body weight 15 minutes prior to PAF challenge. Thirty to fifty µL blood is collected by cutting the tail end into a heparinized micro-hematocrit tube (O.D. 1.50 mm) 15 minutes after PAF administration. All test compounds are given intravenously at 3 mg/kg 15 minutes before PAF (10 ug/kg, intravenously) or AA (0.5 mg/ear) in mice.

EXAMPLE 6

Effect of Compounds on Cytosol 5-Lipoxygenase of Rat Basophile Leukemia Cells (a) Enzyme preparation Washed rat RBL cells (4x108) were suspended in 20 ml of 50M potassium phosphate buffer at pH 7.4 containing 10% ethylene glycol/1 mM EDTA (Buffer A). The cell suspension was sonicated at 20 KHz for 30 seconds, and the sonicate was centrifuged at 10,000×g for 10 minutes, followed by further centrifugation at 105,000×g for 1 hr. The supernatant solution (cytosol fraction) containing 5-lipoxygenase was stored at −70° C. Protein concentration was determined according to the procedure of Bradford (Bradford Dye Reagent) with bovine serum albumin as a standard.

(b) Enzyme assay For routine assay of 5-lipoxygenase the mixture contained 50 mM potassium phosphate buffer at pH 7.4, 2 mM $CaCl_2$, 2 mM ATP, 25M arachidonic acid (0.1 Ci) and enzyme (50–100 mg of protein) in a final volume of 200 L. The reaction was carried out at 24° C. for 3 minutes. The mixture was extracted with 0.2 ml of an ice-cold mixture of ethyl ether:methanol: 0.2M citric acid (30:4:1). The extract was subjected to thin-layer chromatography at −10° C. in a solvent system of petroleum ether:ethyl ether:acetic acid (15:85:0.1). The silica gel zones corresponding to authentic arachidonic acid and its metabolites were scraped into scintillation vials for counting. The enzyme activity was expressed in terms of the amount of arachidonic acid oxygenated for 3 minutes. Representative compounds 9, 11, 14, and 15, identified above, showed activity in this assay.

Modifications and variations of the present invention relating to compounds that reduce the formation of oxygen radicals during an inflammatory or immune response will be obvious to those skilled in the art from the foregoing detailed description of the invention. Such modifications and variations are intended to come within the scope of the appended claims.

We claim:

1. A compound of formula:

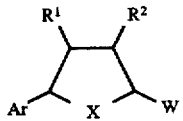

wherein:

Ar is an aryl or heteroaryl group that is optionally substituted with at least one group selected from the group consisting of halo, lower alkoxy, lower aryloxy, —C(O)N(OM)R⁴, A—B, cyano, or R³; but when W is —A—B, Ar is substituted at least once with —C(O)N(OM)R⁴, and is optionally substituted with halo, lower alkoxy, lower aryloxy, A—B, cyano, or R³;

W is independently —C(O)N(OM)R⁴, or —A—B; but when W is —A—B, Ar is substituted at least once with —C(O)N(OM)R⁴, and is optionally substituted with halo, lower alkoxy, lower aryloxy, A—B, cyano, or R³;

A is lower alkyl, lower alkenyl, lower alkynyl, alkaryl or aralkyl groups, wherein one or more carbons optionally can be replaced by O, N, or S; (with valence completed with hydrogen or oxygen as necessary), provided —A— does not form two adjacent heteroatoms;

B is selected from the group consisting of pyridylimidazole and benzimidazole, either of which is optionally substituted with R₃;

M is hydrogen, a pharmaceutically acceptable cation, or a metabolically cleavable leaving group;

X is O, S, S(O), NR⁵, or CHR⁵;

R¹ and R² are independently hydrogen, lower alkyl; halo lower alkyl, halo; and —COOH; and R³ and R⁴ are independently hydrogen or alkyl, alkenyl, alkynyl, aryl, aralkyl, alkaryl, $C_{1-6}$alkoxy-$C_{1-10}$alkyl, $C_{1-6}$alkylthio-$C_{1-10}$alkyl, heteroaryl, or heteroarylalkyl-;

R⁵ is hydrogen, lower alkyl, lower alkenyl, lower alkynyl, alkaryl, —AN(OM)C(O)N(R³)R⁴, —AN(R³)C(O)N(OM)R⁴, —AN(OM)C(O)R⁴, —AC(O)N(OM)R⁴, —AS(O)ₙR³, —AS(O)ₙCH₂C(O)R³, —AS(O)ₙCH₂CH(OH)R³, —AC(O)NHR⁵; and wherein n is 0–2, or pharmaceutically acceptable salt thereof.

2. The compound of claim 1, wherein Ar is selected from the group consisting of phenyl, trimethoxyphenyl, dimethoxyphenyl, fluorophenyl, difluorophenyl, pyridyl, dimethoxypyridyl, quinolinyl, furyl, imidazolyl, and thienyl.

3. The compound of claim 1, wherein Ar is selected from the group consisting of 4-fluorophenyl, 3,4,5-trimethoxyphenyl, 3,4-dimethoxyphenyl, 2,3-dimethoxypyridyl, 3,4-difluorophenyl, 3-quinolinyl, wherein:

$R^1$ and $R^2$ are hydrogen.

4. A pharmaceutical composition comprising an effective amount of the compound of claim 1, or a pharmaceutically acceptable salt thereof, and a pharmaceutically acceptable carrier.

5. A method for the treatment of inflammatory disorders in a host comprising administering an effective amount of a compound of claim 1 or a pharmaceutically acceptable salt thereof.

6. The method of claim 5, wherein the animal is selected from a human, a mammal, an equine, a canine and a bovine.

7. The compound of claim 1 wherein X is O.

8. The compound of claim 1, wherein the aryl group has a halogen substituent.

9. The compound of claim 1 wherein W is —A—B.

10. The compound of claim 9, wherein $R^3$ or $R^4$ are hydrogen.

11. The compound of claim 1, wherein $R^1$ and $R^2$ are hydrogen.

12. The compound of claim 1, wherein A is selected from the group consisting of acetylenyl, propynyl, and —C≡C—CH(alkyl)-.

13. The compound of claim 1, wherein A is lower alkyl-.

14. The compound of claim 1 wherein X is S.

15. The compound of claim 1 wherein the aryl group has a fluorine substituent.

16. The compound of claim 1, wherein W is —C(O)N(OM)$R^4$.

17. The compound of claim 1, wherein A is lower alkenyl.

18. The compound of claim 1, wherein A is lower alkynyl.

19. The compound of claim 1, wherein B is benzimidazole.

20. The method of claim 5, wherein the compound has a W substituent that is —A—B.

21. A compound of formula:

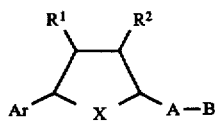

(I)

wherein:

Ar is an aryl or heteroaryl group any of which is substituted at least once with —C(O)N(OM)$R^4$, and is optionally substituted with halo, lower alkoxy, lower aryloxy, A—B, cyano, or $R^3$;

A is lower alkyl, lower alkenyl, lower alkynyl, alkaryl or aralkyl groups, wherein one or more carbons optionally can be replaced by O, N, or S; (with valence completed with hydrogen or oxygen as necessary), provided —A— does not form two adjacent heteroatoms;

B is selected from the group consisting of pyridylimidazole and benzimidazole, either of which is optionally substituted with $R_3$;

M is hydrogen, a pharmaceutically acceptable cation, or a metabolically cleavable leaving group;

X is O, S, S(O);

$R^1$ and $R^2$ are independently hydrogen, lower alkyl; halo lower alkyl; halo; and —COOH; and $R^3$ and $R^4$ are independently hydrogen or alkyl, alkenyl, alkynyl, aryl, aralkyl, alkaryl, $C_{1-6}$alkoxy-$C_{1-10}$alkyl, $C_{1-6}$alkylthio-$C_{1-10}$alkyl, heteroaryl, or heteroarylalkyl; or pharmaceutically acceptable salt thereof.

22. The compound of claim 21 wherein —A—B is

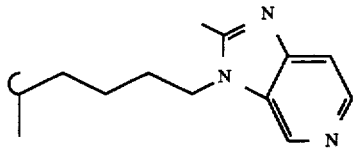

and wherein Ar is aryl or heteroaryl, any of which group is substituted at least once with —C(O)N(OM)$R^4$, and is optionally substituted with halo, alkoxy, aryloxy, or cyano.

23. The compound of claim 21, wherein —A—B is

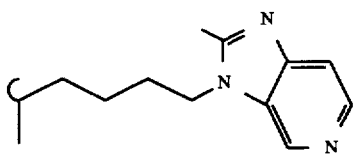

and wherein Ar is aryl or heteroaryl substituted at least once —C(O)N(OM)$R^4$.

24. A pharmaceutical composition comprising an effective amount of the compound of claim 21 or a pharmaceutically acceptable salt thereof, and a pharmaceutically acceptable carrier.

25. A pharmaceutical composition comprising an effective amount of the compound of claim 23 or a pharmaceutically acceptable salt thereof, and a pharmaceutically acceptable carrier.

26. A method for the treatment of inflammatory disorders in a host comprising administering an effective amount of a compound of claim 21 or a pharmaceutically acceptable salt thereof.

27. A method for the treatment of inflammatory disorders in a host comprising administering an effective amount of a compound of claim 22 or a pharmaceutically acceptable salt thereof.

28. A method for the treatment of inflammatory disorders in a host comprising administering an effective amount of a compound of claim 23 or a pharmaceutically acceptable salt thereof.

29. A method for the treatment of inflammatory disorders in a host comprising administering an effective amount of a compound of any of claims 7–10, or 12–19, or a pharmaceutically acceptable salt thereof.

30. A method for the treatment of inflammatory disorders in a host comprising administering an effective amount of a compound of claim 21 or a pharmaceutically acceptable salt thereof.

* * * * *